United States Patent
Bukshtab et al.

(10) Patent No.: US 10,114,205 B2
(45) Date of Patent: Oct. 30, 2018

(54) MULTIPASS VIRTUALLY IMAGED PHASED ARRAY ETALON

(71) Applicant: Avedro, Inc., Waltham, MA (US)

(72) Inventors: Michael A. Bukshtab, Boston, MA (US); Marc D. Friedman, Needham, MA (US)

(73) Assignee: Avedro, Inc., Waltham, MA (US)

( * ) Notice: Subject to any disclaimer, the term of this patent is extended or adjusted under 35 U.S.C. 154(b) by 166 days.

(21) Appl. No.: 14/941,214

(22) Filed: Nov. 13, 2015

(65) Prior Publication Data

US 2016/0139390 A1 May 19, 2016

Related U.S. Application Data

(60) Provisional application No. 62/079,544, filed on Nov. 13, 2014.

(51) Int. Cl.
*A61B 3/14* (2006.01)
*G01J 3/00* (2006.01)
(Continued)

(52) U.S. Cl.
CPC ............ *G02B 21/0056* (2013.01); *A61B 3/13* (2013.01); *A61B 3/14* (2013.01); *A61B 5/0068* (2013.01);
(Continued)

(58) Field of Classification Search
CPC ............ G02B 21/0056; G02B 21/0048; G02B 17/006; A61B 3/13; A61B 3/14;
(Continued)

(56) References Cited

U.S. PATENT DOCUMENTS

| | | |
|---|---|---|
| 3,169,459 A | 2/1965 | Friedberg et al. |
| 4,034,750 A | 7/1977 | Seiderman |
| (Continued) | | |

FOREIGN PATENT DOCUMENTS

| | | |
|---|---|---|
| DE | 102008046834 | 3/2010 |
| EP | 1285679 | 2/2003 |
| (Continued) | | |

OTHER PUBLICATIONS

Wollensak G., et al., "Cross-linking of Scleral Collagen in the Rabbit Using Riboflavin and UVA," Acta Ophtalmologica Scandinavica, vol. 83(4), pp. 477-482; Aug. 2005 (6 pages).
(Continued)

*Primary Examiner* — Collin X Beatty
(74) *Attorney, Agent, or Firm* — McDonnell Boehnen Hulbert & Berghoff LLP

(57) ABSTRACT

An example system determines biomechanical properties of eye tissue. The system includes a confocal microscopy system configured to scan the incident light across a plurality of cross-sections of the tissue. The incident light is reflected by the plurality of cross-sections of tissue as scattered light. The system includes a spectrometer to receive the scattered light and provide spectral information for the scattered light. The system includes processor(s) to determine a Brillouin frequency shift from the spectral information and to generate a three-dimensional profile of the corneal tissue according to the Brillouin frequency shift. The three-dimensional profile provides an indicator of one or more biomechanical properties of the tissue. The spectrometer includes a multipass optical device that generates an interference pattern from the scattered light. The interference pattern provides the spectral information for the scattered light. The spectrometer includes a camera to detect the interference pattern from the optical device.

20 Claims, 10 Drawing Sheets

(51) Int. Cl.
*G02F 1/01* (2006.01)
*G02B 27/00* (2006.01)
*G02B 1/10* (2015.01)
*G02B 5/28* (2006.01)
*G02B 21/00* (2006.01)
*A61B 5/00* (2006.01)
*G01B 9/02* (2006.01)
*A61B 3/13* (2006.01)
*G02B 17/00* (2006.01)

(52) U.S. Cl.
CPC ........ *A61B 5/0075* (2013.01); *G01B 9/02044* (2013.01); *G01J 3/00* (2013.01); *G02B 17/006* (2013.01); *G02B 21/0048* (2013.01)

(58) Field of Classification Search
CPC ... A61B 5/7257; A61B 5/0075; A61B 5/0068; A61B 18/22; G01J 3/00; G01J 3/26; G01B 9/02044; G01B 9/02007
USPC ......... 351/206, 246; 356/300; 359/279, 577, 359/584, 588–589
See application file for complete search history.

(56) References Cited

U.S. PATENT DOCUMENTS

| | | |
|---|---|---|
| 4,161,013 A | 7/1979 | Grodzinsky et al. |
| 4,326,529 A | 4/1982 | Doss et al. |
| 4,381,007 A | 4/1983 | Doss |
| 4,665,913 A | 5/1987 | L'Esperance, Jr. |
| 4,712,543 A | 12/1987 | Baron |
| 4,764,007 A | 8/1988 | Task |
| 4,805,616 A | 2/1989 | Pao |
| 4,881,543 A | 11/1989 | Trembly et al. |
| 4,891,043 A | 1/1990 | Zeimer et al. |
| 4,969,912 A | 11/1990 | Kelman et al. |
| 4,994,058 A | 2/1991 | Raven et al. |
| 5,016,615 A | 5/1991 | Driller et al. |
| 5,019,074 A | 5/1991 | Muller |
| 5,098,426 A | 3/1992 | Sklar et al. |
| 5,103,005 A | 4/1992 | Gyure et al. |
| 5,171,254 A | 12/1992 | Sher |
| 5,171,318 A | 12/1992 | Gibson et al. |
| 5,270,792 A * | 12/1993 | Snyder ............... F03G 7/06 356/520 |
| 5,281,211 A | 1/1994 | Parel et al. |
| 5,332,802 A | 7/1994 | Kelman et al. |
| 5,450,144 A | 9/1995 | Ben Nun |
| 5,461,212 A | 10/1995 | Seiler et al. |
| 5,490,849 A | 2/1996 | Smith |
| 5,512,966 A | 4/1996 | Snook |
| 5,562,656 A | 10/1996 | Sumiya |
| 5,608,472 A | 3/1997 | Szirth et al. |
| 5,618,284 A | 4/1997 | Sand |
| 5,624,437 A | 4/1997 | Freeman et al. |
| 5,634,921 A | 6/1997 | Hood et al. |
| 5,766,171 A | 6/1998 | Silvestrini |
| 5,779,696 A | 7/1998 | Berry et al. |
| 5,786,893 A | 7/1998 | Fink et al. |
| 5,814,040 A | 9/1998 | Nelson et al. |
| 5,885,275 A | 3/1999 | Muller |
| 5,891,131 A | 4/1999 | Rajan et al. |
| 5,910,110 A | 6/1999 | Bastable |
| 6,033,396 A | 3/2000 | Huang et al. |
| 6,099,521 A | 8/2000 | Shadduck |
| 6,101,411 A | 8/2000 | Newsome |
| 6,104,959 A | 8/2000 | Spertell |
| 6,139,876 A | 10/2000 | Kolta |
| 6,161,544 A | 12/2000 | DeVore et al. |
| 6,162,210 A | 12/2000 | Shadduck |
| 6,188,500 B1 | 2/2001 | Rudeen et al. |
| 6,218,360 B1 | 4/2001 | Cintron et al. |
| 6,223,075 B1 | 4/2001 | Beck et al. |
| 6,270,221 B1 | 8/2001 | Liang et al. |
| 6,280,436 B1 | 8/2001 | Freeman et al. |
| 6,293,938 B1 | 9/2001 | Muller et al. |
| 6,319,273 B1 | 11/2001 | Chen et al. |
| 6,322,557 B1 | 11/2001 | Nikolaevich et al. |
| 6,325,792 B1 | 12/2001 | Swinger et al. |
| 6,334,074 B1 | 12/2001 | Spertell |
| 6,342,053 B1 | 1/2002 | Berry |
| 6,394,999 B1 | 5/2002 | Williams et al. |
| 6,402,739 B1 | 6/2002 | Neev |
| 6,413,255 B1 | 7/2002 | Stern |
| 6,478,792 B1 | 11/2002 | Hansel |
| 6,520,956 B1 | 2/2003 | Huang |
| 6,520,958 B1 | 2/2003 | Shimmick et al. |
| 6,537,545 B1 | 3/2003 | Karageozian et al. |
| 6,571,118 B1 | 5/2003 | Utzinger et al. |
| 6,572,849 B1 | 6/2003 | Shahinian, Jr. |
| 6,617,963 B1 | 9/2003 | Watters et al. |
| 6,673,067 B1 | 1/2004 | Peyman |
| 6,918,904 B1 | 7/2005 | Peyman |
| 6,946,440 B1 | 9/2005 | DeWoolfson et al. |
| 7,001,374 B2 | 2/2006 | Peyman |
| 7,004,902 B2 | 2/2006 | Luce |
| 7,044,945 B2 | 5/2006 | Sand |
| 7,073,510 B2 | 7/2006 | Redmond et al. |
| 7,130,835 B2 | 10/2006 | Cox et al. |
| 7,141,049 B2 | 11/2006 | Stern et al. |
| 7,192,429 B2 | 3/2007 | Trembly |
| 7,237,898 B1 | 7/2007 | Hohla et al. |
| 7,270,658 B2 | 9/2007 | Woloszko et al. |
| 7,302,189 B2 | 11/2007 | Kawahata |
| 7,331,350 B2 | 2/2008 | Kochevar et al. |
| 7,402,562 B2 | 7/2008 | DeWoolfson et al. |
| 7,753,943 B2 | 7/2010 | Strong |
| 7,871,378 B1 | 1/2011 | Chou et al. |
| 7,898,656 B2 | 3/2011 | Yun et al. |
| 7,935,058 B2 | 5/2011 | Dupps, Jr. et al. |
| 8,111,394 B1 | 2/2012 | Borysow et al. |
| 8,115,919 B2 | 2/2012 | Yun et al. |
| 8,366,689 B2 | 2/2013 | Marshall et al. |
| 8,414,911 B2 | 4/2013 | Mattson et al. |
| 8,475,437 B2 | 7/2013 | Mrochen et al. |
| 8,574,277 B2 | 11/2013 | Muller et al. |
| 8,715,273 B2 | 5/2014 | Thyzel |
| 8,995,618 B2 | 3/2015 | Gertner |
| 9,005,261 B2 | 4/2015 | Brinkmann |
| 2001/0041856 A1 | 11/2001 | McDaniel |
| 2001/0047012 A1 | 11/2001 | Desantis, Jr. |
| 2001/0055095 A1 | 12/2001 | D'Souza et al. |
| 2002/0002369 A1 | 1/2002 | Hood |
| 2002/0013577 A1 | 1/2002 | Frey et al. |
| 2002/0042638 A1 | 4/2002 | Iezzi et al. |
| 2002/0049437 A1 | 4/2002 | Silvestrini |
| 2002/0099363 A1 | 7/2002 | Woodward et al. |
| 2002/0159618 A1 | 10/2002 | Freeman et al. |
| 2002/0164379 A1 | 11/2002 | Nishihara et al. |
| 2003/0018255 A1 | 1/2003 | Martin et al. |
| 2003/0030908 A1 | 2/2003 | Cheng et al. |
| 2003/0135122 A1 | 7/2003 | Bambot et al. |
| 2003/0175259 A1 | 9/2003 | Karageozian et al. |
| 2003/0189689 A1 | 10/2003 | Rathjen |
| 2003/0208190 A1 | 11/2003 | Roberts et al. |
| 2003/0216728 A1 | 11/2003 | Stern et al. |
| 2003/0231285 A1 | 12/2003 | Ferguson |
| 2004/0001821 A1 | 1/2004 | Silver et al. |
| 2004/0002694 A1 | 1/2004 | Pawlowski et al. |
| 2004/0071778 A1 | 4/2004 | Bellmann et al. |
| 2004/0093046 A1 | 5/2004 | Sand |
| 2004/0111086 A1 | 6/2004 | Trembly |
| 2004/0143250 A1 | 7/2004 | Trembly |
| 2004/0199079 A1 | 10/2004 | Chuck et al. |
| 2004/0199158 A1 | 10/2004 | Hood et al. |
| 2004/0204707 A1 | 10/2004 | Hood et al. |
| 2004/0243160 A1 | 12/2004 | Shiuey et al. |
| 2004/0254520 A1 | 12/2004 | Porteous et al. |
| 2005/0038471 A1 | 2/2005 | Chan et al. |
| 2005/0096515 A1 | 5/2005 | Geng |
| 2005/0149006 A1 | 7/2005 | Peyman |
| 2005/0187599 A1 | 8/2005 | Sharkey et al. |
| 2005/0271590 A1 | 12/2005 | Schwartz et al. |

(56) References Cited

U.S. PATENT DOCUMENTS

| | | |
|---|---|---|
| 2006/0058592 A1 | 3/2006 | Bouma et al. |
| 2006/0106371 A1 | 5/2006 | Muhlhoff et al. |
| 2006/0135957 A1 | 6/2006 | Panescu |
| 2006/0149343 A1 | 7/2006 | Altshuler et al. |
| 2006/0177430 A1 | 8/2006 | Bhushan et al. |
| 2006/0189964 A1 | 8/2006 | Anderson et al. |
| 2006/0195074 A1 | 8/2006 | Bartoli |
| 2006/0195076 A1 | 8/2006 | Blumenkranz et al. |
| 2006/0276777 A1 | 12/2006 | Coroneo |
| 2006/0287662 A1 | 12/2006 | Berry et al. |
| 2007/0024860 A1 | 2/2007 | Tobiason et al. |
| 2007/0027509 A1 | 2/2007 | Eisenberg et al. |
| 2007/0028928 A1 | 2/2007 | Peyman |
| 2007/0048340 A1 | 3/2007 | Ferren et al. |
| 2007/0055227 A1 | 3/2007 | Khalaj et al. |
| 2007/0074722 A1 | 4/2007 | Giroux et al. |
| 2007/0090153 A1 | 4/2007 | Naito et al. |
| 2007/0099966 A1 | 5/2007 | Fabricant |
| 2007/0123845 A1 | 5/2007 | Lubatschowski |
| 2007/0135805 A1 | 6/2007 | Peyman |
| 2007/0142828 A1 | 6/2007 | Peyman |
| 2007/0161976 A1 | 7/2007 | Trembly |
| 2007/0203478 A1 | 8/2007 | Herekar |
| 2007/0203547 A1 | 8/2007 | Costello et al. |
| 2007/0244470 A1 | 10/2007 | Barker, Jr. et al. |
| 2007/0244496 A1 | 10/2007 | Hellenkamp |
| 2007/0265603 A1 | 11/2007 | Pinelli |
| 2008/0009901 A1 | 1/2008 | Redmond et al. |
| 2008/0015660 A1 | 1/2008 | Herekar |
| 2008/0027328 A1 | 1/2008 | Klopotek et al. |
| 2008/0033408 A1 | 2/2008 | Bueler et al. |
| 2008/0063627 A1 | 3/2008 | Stucke et al. |
| 2008/0114283 A1 | 5/2008 | Mattson et al. |
| 2008/0139671 A1 | 6/2008 | Herekar |
| 2008/0208177 A1 | 8/2008 | Mrochen et al. |
| 2009/0024117 A1 | 1/2009 | Muller |
| 2009/0054879 A1 | 2/2009 | Berry |
| 2009/0069798 A1 | 3/2009 | Muller et al. |
| 2009/0116096 A1 | 5/2009 | Zalevsky et al. |
| 2009/0130176 A1 | 5/2009 | Bossy-Nobs et al. |
| 2009/0149842 A1 | 6/2009 | Muller et al. |
| 2009/0149923 A1 | 6/2009 | Herekar |
| 2009/0171305 A1 | 7/2009 | El Hage |
| 2009/0192437 A1 | 7/2009 | Soltz et al. |
| 2009/0209954 A1 | 8/2009 | Muller et al. |
| 2009/0234335 A1 | 9/2009 | Yee |
| 2009/0271155 A1 | 10/2009 | Dupps, Jr. et al. |
| 2009/0275929 A1 | 11/2009 | Zickler |
| 2009/0276042 A1 | 11/2009 | Hughes et al. |
| 2010/0028407 A1 | 2/2010 | Del Priore et al. |
| 2010/0036488 A1 | 2/2010 | de Juan, Jr. et al. |
| 2010/0057060 A1 | 3/2010 | Herekar |
| 2010/0069894 A1 | 3/2010 | Mrochen et al. |
| 2010/0082018 A1 | 4/2010 | Panthakey et al. |
| 2010/0094197 A1 | 4/2010 | Marshall et al. |
| 2010/0114109 A1 | 5/2010 | Peyman |
| 2010/0149487 A1 | 6/2010 | Ribak |
| 2010/0173019 A1 | 7/2010 | Paik et al. |
| 2010/0189817 A1 | 7/2010 | Krueger et al. |
| 2010/0191228 A1 | 7/2010 | Ruiz et al. |
| 2010/0203103 A1 | 8/2010 | Dana et al. |
| 2010/0204584 A1 | 8/2010 | Omberg et al. |
| 2010/0210996 A1 | 8/2010 | Peyman |
| 2010/0271593 A1 | 10/2010 | Filar |
| 2010/0286156 A1 | 11/2010 | Pinelli |
| 2010/0317588 A1 | 12/2010 | Shoseyov et al. |
| 2010/0318017 A1 | 12/2010 | Lewis et al. |
| 2011/0044902 A1 | 2/2011 | Weiner et al. |
| 2011/0077624 A1 | 3/2011 | Brady et al. |
| 2011/0098790 A1 | 4/2011 | Daxer |
| 2011/0118654 A1 | 5/2011 | Muller et al. |
| 2011/0125076 A1 | 5/2011 | Kraft et al. |
| 2011/0152219 A1 | 6/2011 | Stagni |
| 2011/0190742 A1 | 8/2011 | Anisimov |
| 2011/0202114 A1 | 8/2011 | Kessel et al. |
| 2011/0208300 A1 | 8/2011 | de Juan, Jr. et al. |
| 2011/0237999 A1 | 9/2011 | Muller et al. |
| 2011/0264082 A1 | 10/2011 | Mrochen et al. |
| 2011/0288466 A1 | 11/2011 | Muller et al. |
| 2011/0301524 A1 | 12/2011 | Bueler et al. |
| 2012/0083772 A1 | 4/2012 | Rubinfeld et al. |
| 2012/0140238 A1 | 6/2012 | Horn et al. |
| 2012/0203051 A1 | 8/2012 | Brooks et al. |
| 2012/0203161 A1 | 8/2012 | Herekar |
| 2012/0209051 A1 | 8/2012 | Blumenkranz et al. |
| 2012/0215155 A1 | 8/2012 | Muller et al. |
| 2012/0283621 A1 | 11/2012 | Muller |
| 2012/0289886 A1 | 11/2012 | Muller et al. |
| 2012/0302862 A1 | 11/2012 | Yun et al. |
| 2012/0303008 A1 | 11/2012 | Muller et al. |
| 2012/0310083 A1 | 12/2012 | Friedman et al. |
| 2012/0310223 A1 | 12/2012 | Knox et al. |
| 2013/0060187 A1 | 3/2013 | Friedman et al. |
| 2013/0085370 A1 | 4/2013 | Friedman et al. |
| 2013/0116757 A1 | 5/2013 | Russmann |
| 2013/0245536 A1 | 9/2013 | Friedman et al. |
| 2013/0310732 A1 | 11/2013 | Foschini et al. |
| 2014/0066835 A1 | 3/2014 | Muller et al. |
| 2014/0194957 A1 | 7/2014 | Rubinfeld et al. |
| 2014/0249509 A1 | 9/2014 | Rubinfeld et al. |
| 2014/0276361 A1 | 9/2014 | Herekar et al. |
| 2014/0277431 A1 | 9/2014 | Herekar et al. |
| 2014/0343480 A1 | 11/2014 | Kamaev et al. |
| 2014/0368793 A1 | 12/2014 | Friedman et al. |
| 2015/0085252 A1 | 3/2015 | Fujimura et al. |
| 2016/0175442 A1 | 6/2016 | Kamaev et al. |

FOREIGN PATENT DOCUMENTS

| | | |
|---|---|---|
| EP | 2253321 | 11/2010 |
| KG | 1376 | 8/2011 |
| RU | 2086215 | 8/1997 |
| RU | 2098057 | 12/1997 |
| RU | 2121825 | 11/1998 |
| RU | 2127099 | 3/1999 |
| RU | 2127100 | 3/1999 |
| RU | 2309713 | 11/2007 |
| RU | 2359716 | 6/2009 |
| RU | 2420330 | 6/2011 |
| RU | 2428152 | 9/2011 |
| RU | 2456971 | 7/2012 |
| WO | 93/16631 | 9/1993 |
| WO | 94/03134 | 2/1994 |
| WO | 00/74648 | 12/2000 |
| WO | 01/58495 | 8/2001 |
| WO | 03/061696 | 7/2003 |
| WO | 2004/052223 | 6/2004 |
| WO | 2005/110397 | 11/2005 |
| WO | 2006/012947 | 2/2006 |
| WO | 2006/128038 | 11/2006 |
| WO | 2007/001926 | 1/2007 |
| WO | 2007/053826 | 5/2007 |
| WO | 2007/081750 | 7/2007 |
| WO | 2007/120457 | 10/2007 |
| WO | 2007/128581 | 11/2007 |
| WO | 2007/139927 | 12/2007 |
| WO | 2007/143111 | 12/2007 |
| WO | 2008/000478 | 1/2008 |
| WO | 2008/052081 | 5/2008 |
| WO | 2008/095075 | 8/2008 |
| WO | 2009/042159 | 4/2009 |
| WO | 2009/073213 | 6/2009 |
| WO | 2009/114513 | 9/2009 |
| WO | 2009/146151 | 12/2009 |
| WO | 2010/011119 | 1/2010 |
| WO | 2010/015255 | 2/2010 |
| WO | 2010/023705 | 3/2010 |
| WO | 2010/039854 | 4/2010 |
| WO | 2010/093908 | 8/2010 |
| WO | 2011/019940 | 2/2011 |
| WO | 2011/050360 | 4/2011 |
| WO | 2011/116306 | 9/2011 |
| WO | 2012/004726 | 1/2012 |
| WO | 2012/047307 | 4/2012 |

(56) References Cited

FOREIGN PATENT DOCUMENTS

| WO | 2012/149570 | 11/2012 |
|---|---|---|
| WO | 2012/158991 | 11/2012 |
| WO | 2012/174453 | 12/2012 |
| WO | 2013/062910 | 5/2013 |
| WO | 2013/148713 | 10/2013 |
| WO | 2013/148896 | 10/2013 |
| WO | 2013/149075 | 10/2013 |
| WO | 2014/081875 | 5/2014 |
| WO | 2014/145666 | 9/2014 |
| WO | 2014/202736 | 12/2014 |
| WO | 2016069628 | 5/2016 |

OTHER PUBLICATIONS

Wollensak G., "Crosslinking Treatment of Progressive Keratoconus: New Hope," Current Opinion in Ophthalmology, vol. 17(4), pp. 356-360; Aug. 2006 (5 pages).

Wollensak G., et al., "Hydration Behavior of Porcine Cornea Crosslinked with Riboflavin and Ultraviolet," A.J. Cataract Refract. Surg., vol. 33, Issue 3, pp. 516-521; Mar. 2007 (6 pages).

Wollensak G., et al., "Riboflavin/Ultraviolet-A-induced Collagen Crosslinking for the Treatment of Keratoconus," American Journal of Ophthalmology, vol. 135, No. 5, pp. 620-627; May 2003 (8 pages).

Wollensak, G. et al. "Laboratory Science: Stress-Strain Measurements of Human and Porcine Corneas after Riboflavin-Ultraviolet-A-Induced Cross-Linking." Journal of Cataract and Refractive Surgery. vol. 29, No. 9, Sep. 2003 (pp. 1780-1785).

Wong, J. et al., "Post-Lasik ectasia: PRK following previous stablization and effective management with Riboflavin / ultraviolet A-induced collagen cross-linking," Association for Research in Vision and Ophthalmology, 2006 (1 page).

Yang H., et al., "3-D Histomorphometry of the Normal and Early Glaucomatous Monkey Optic Nerve Head: Lamina Cribrosa and Peripapillary Scleral Position and Thickness," Investigative Ophthalmology & Visual Science, vol. 48, No. 10, pp. 4597-4607; Oct. 2007 (11 pages).

Yang N., Oster G. Dye-sensitized photopolymerization in the presence of reversible oxygen carriers. J. Phys. Chem. 74, 856-860 (1970) (5 pages).

Zhang, Y. et al., "Effect of the Synthetic NC-1059 Peptide on Diffusion of Riboflavin Across an Intact Corneal Epithelium", May 6, 2012, ARBO 2012 Annual Meeting Abstract, 140 Stroma and Keratocytes, program No. 1073, poster board No. A109.

Zhang, Y. et al., "Effects of Ultraviolet-A and Riboflavin on the Interaction of Collagen and Proteoglycans during Corneal Cross-linking", Journal of Biological Chemistry, vol. 286, No. 15, dated Apr. 15, 2011 (pp. 13011-13022).

Zderic V., et al., "Drug Delivery Into the Eye With the Use of Ultrasound," J. Ultrasound Med, vol. 23(10), pp. 1349-1359; Oct. 2004 (11 pages).

Zderic V., et al., "Ultrasound-enhanced Transcorneal Drug Delivery," Cornea vol. 23, No. 8, pp. 804-811; Nov. 2004 (8 pages).

Abahussin, M. "3D Collagen Orientation Study of the Human Cornea Using X-ray Diffraction and Femtosecond Laser Technology" Investigative Ophthalmology & Visual Science, Nov. 2009, vol. 50, No. 11, pp. 5159-5164.

Acosta A. et al., "Corneal Stroma Regeneration in Felines After Supradescemetic Keratoprothesis Implantation," Cornea, vol. 25, No. 7, pp. 830-838; Aug. 2006.

Baier J. et al., "Singlet Oxygen Generation by UVA Light Exposure of Endogenous Photosensitizers," Biophysical Journal, vol. 91(4), pp. 1452-1459; Aug. 15, 2006.

Ballou, D. et al., "Direct Demonstration of Superoxide Anion Production During the Oxidation of Reduced Flavin and of Its Catalytic Decomposition by Erythrocuprein," Biochemical and Biophysical Research Communications vol. 36, No. 6, pp. 898-904, Jul. 11, 1969.

Barbarino, S. et al., "Post-LASIK ectasia: Stabilization and Effective Management with Riboflavin / ultraviolet A-induced collagen cross-linking," Association for Research in Vision and Ophthalmology, 2006.

Berjano E., et al., "Radio-Frequency Heating of the Cornea: Theoretical Model and In Vitro Experiments," IEEE Transactions on Biomedical Engineering, vol. 49, No. 3, pp. 196-205; Mar. 2002.

Berjano E., et al., "Ring Electrode for Radio-frequency Heating of the Cornea: Modelling and in vitro Experiments," Medical & Biological Engineering & Computing, vol. 41, pp. 630-639; Jun. 2003.

Brüel, A., "Changes in Biomechanical Properties, Composition of Collagen and Elastin, and Advanced Glycation Endproducts of the Rat Aorta in Relation to Age," Atherosclerosis 127, Mar. 14, 1996.

Chai, D. et al., "Quantitative Assessment of UVA-Riboflavin Corneal Cross-Linking Using Nonlinear Optical Microscopy," Investigative Ophthalmology & Visual Science, Jun. 2011, vol. 52, No. 7, 4231-4238.

Chan B.P., et al., "Effects of photochemical crosslinking on the microstructure of collagen and a feasibility study on controlled protein release;" Acta Biomaterialia, vol. 4, Issue 6, pp. 1627-1636; Jul. 1, 2008.

Chandonnet, "CO2 Laser Annular Thermokeratoplasty: A Preliminary Study," Lasers in Surgery and Medicine, vol. 12, pp. 264-273; 1992.

Chace, K.V. et al., Abstract for "The role of nonenzymatic glycosylation, transition metals, and free radicals in the formation of collagen aggregates", Arch Biochem Biophys., Aug. 1, 1991, 288(2), pp. 473-480.

Clinical Trials.gov, "Riboflavin Mediated Corneal Crosslinking for Stabilizing Progression of Keratoconus (CCL)," University Hospital Freiburg, Feb. 20, 2008; retrieved from http://www.clinicaltrials.gov/ct2/show/NCT00626717, on Apr. 26, 2011.

Corbett M., et al., "Effect of Collagenase Inhibitors on Corneal Haze after PRK," Exp. Eye Res., vol. 72, Issue 3, pp. 253-259; Jan. 2001.

Coskenseven E. et al., "Comparative Study of Corneal Collagen Cross-linking With Riboflavin and UVA Irradiation in Patients With Keratoconus," Journal of Refractive Surgery, vol. 25, issue 4, pp. 371-376; Apr. 2009.

"Definity (perflutren) injection, suspension [Bristol-Myers Squibb Medical Imaging]," http://dailymed.nlm.nih.gov/dailymed/drugInfo.cfm?id=8338, revised Sep. 2008, retrieved via the internet archive from http://web.archive.org/web/20100321105500/http://dailymed.nlm.nih.gov/dailymed/drugInfo.cfm?id=8338, on Dec. 14, 2011.

Ehlers W., et al., "Factors Affecting Therapeutic Concentration of Topical Aminocaproic Acid in Traumatic Hyphema," Investigative Ophthalmology & Visual Science, vol. 31, No. 11, pp. 2389-2394; Nov. 1990.

Erskine H., "Avedro Becomes Sponsor of US FDA Clinical Trials of Corneal Collagen Crosslinking," Press Release, Mar. 16, 2010 (1 page).

Fite et al., "Noninvasive Multimodal Evaluation of Bioengineered Cartilage Constructs Combining Time-Resolved Fluorescence and Ultrasound Imaging." Tissue Eng: Part C vol. 17, No. 4, 2011.

Friedman, M. et al. "Advanced Corneal Cross-Linking System with Fluorescence Dosimetry", Journal of Ophthalmology, vol. 2012, Article ID 303459, dated May 7, 2012.

Frucht-Pery, et al. "Iontophoresis—gentamicin delivery into the rabbit cornea, using a hydrogel delivery probe," Jun. 20, 2003.

Gibson, Q. et al., "The Oxidation of Reduced Flavin Mononucleotide by Molecular Oxygen," Biochem. J. (1962) 83, 368-377.

Givens et al. "A Photoactivated Diazpryruvoyl Cross-Linking Agent for Bonding Tissue Containing Type-I Collagen." Photochemistry and Photobiology. vol. 78, No. 1, 2003 (pp. 23-29).

Glenn J.V., et al., "Advanced Glycation End Product (AGE) Accumulation on Bruch's Membrane: Links to Age-Related RPE Dysfunction;" Investigative Ophthalmology & Visual Science, vol. 50, No. 1, pp. 441-451; Jan. 2009.

Gravitz L., "Laser Show in the Surgical Suite: Lasers and a century-old dye could supplant needles and thread;" technology review, MIT, Mar./Apr. 2009; retrieved from http://www.technologyreview.com/biomedicine/22088/?nlid=1767, on Sep. 26, 2011.

(56) References Cited

OTHER PUBLICATIONS

Hafezi F., et al., "Collagen Crosslinking with Ultraviolet-A and Hypoosmolar Riboflavin Solution in Thin Corneas," J. Catract Refract. Surg., vol. 35, No. 1, pp. 621-624; Apr. 2009.
Hammer Arthur et al., "Corneal Biomechanical Properties at different Corneal Cross-Linking (CXL) Irradiances," IOVS, May 2014, vol. 55, No. 5, pp. 2881-2884.
Hitzenberger et al., "Birefringence Properties of the Human Cornea Measured With Polarization Sensitive Optical Coherence Tomography," Bull. Soc. Beige Ophtalmol., 302, 153-168, 2006.
Holmström, B. et al., "Riboflavin As an Electron Donor in Photochemical Reactions," 1867-1871, Nov. 29, 1960.
How to Use Definity: "Frequently Asked Questions;" retrieved from http://www.definityimaging.com/how-faq.html, on Sep. 26, 2011 (3 pages) (date unknown, prior to Apr. 26, 2010).
IMEX, "KXL System: Crosslinking Para Cirugia Corneal Bibliografia Cientifica," Product Literature, Nov. 23, 2010.
Kamaev et al., "Photochemical Kinetics of Corneal Cross-Linking With Riboflavin," Investigative Ophthalmology & Visual Science, Apr. 2012, vol. 53, No. 4, pp. 2360-2367 (8 pages).
Kampik D. et al., "Influence of Corneal Collagen Crosslinking With Riboflavin and Ultraviolet-A Irradiation on Excimer Laser Surgery," Investigative Ophthalmology & Visual Science, vol. 51, No. 8, pp. 3929-3934; Aug. 2010.
Kanellopoulos, A. J., "Collagen Cross-linking in Early Keratoconus With Riboflavin in a Femtosecond Laser-created Pocket: Initial Clinical Results", Journal of Refractive Surgery, Aug. 18, 2009.
Kanellopoulos, A. J., "Keratoconus management: UVA-induced collagen cross-linking followed by a limited topo-guided surface excimer ablation," American Academy of Ophthalmology, 2006 (25 pages).
Kanellopoulos, A. J., "Ultraviolet A cornea collagen cross-linking, as a pre-treatment for surface excimer ablation in the management of keratoconus and post-LASIK ectasia," American Academy of Ophthalmology, 2005 (28 pages).
Kissner Anja, et al. "Pharmacological Modification of the Epithelial Permeability by Benzalkonium Chloride in UVA/Riboflavin Corneal Collagen Cross-Linking," Current Eye Research 35(8), pp. 715-721; Mar. 2010 (7 pages).
Koller, T. et. al., "Complication and failure rates after corneal crosslinking," Journal Cataract and refractive surgery, vol. 35, No. 8, Aug. 2009, pp. 1358-1362.
Koller T., et al., "Therapeutische Quervernetzung der Hornhaut mittels UVA and Riboflavin: Therapeutic Cross-Linking of the Cornea Using Riboflavin/UVA," Klinische Monatsblatter für Augenheilkunde, vol. 224, No. 9, pp. 700-706; Sep. 2007 (7 pages).
Kornilovsky, I. M. "Novye neinvazivnye tekhnologii lazernoy modifikatsii optiko-refraksionnykk struktur glaza. Refraktsionnaya khirurgiya I oftalmologiya." vol. 9, No. 3, 2006 (pp. 17-26).
Krueger, Ronald R., "Rapid VS Standard Collagen CXL with Equivalent Energy Dosing," presentation slides; available at http://www.slideshare.net/logen/krueger-herekar-rapid-cross-linking (date unknown, prior to Nov. 9, 2009) (26 pages).
Massey, V., "Activation of Molecular Oxygen by Flavins and Flavoproteins," The Journal of Biological Chemistry vol. 269, No. 36, Issue of Sep. 9, pp. 22459-22462, 1994 (4 pages).
Marzouky, et. al., Tensioactive-mediated Transepithelial Corneal Cross-linking—First Laboratory Report, European Ophthalmic Review, 2009, 3(2), pp. 67-70.
Lee et al., "Spectrally filtered Raman / Thomson scattering using a rubidium Vapor filter", AIAA J. 40, pp. 2504-2510 (2002).
Li, C. et al. "Elastic Properties of Soft Tissue-Mimicking Phantoms Assessed by Combined Use of Laser Ultrasonics and Low Coherence Interferometry." Optics Express. vol. 19, No. 11, May 9, 2011 (pp. 10153-10163).
Li, C. et al."Noncontact All-Optical Measurement of Corneal Elasticity." Optics Letters. vol. 37, No. 10, May 15, 2012 (pp. 1625-1627).
Li, P. et al. "In Vivo Microstructural and Microvascular Imaging of the Human Corneo-Scleral Limbus Using Optical Coherence Tomography." Biomedical Optics Express. vol. 2, No. 11, Oct. 18, 2011 (pp. 3109-3118).
Meek, K.M. et al. "The Cornea and Scleera", Collagen: Structure and Mechanics, Chapter 13, pp. 359-396, 2008 (38 pages).
Mi S., et al., "The adhesion of LASIK-like flaps in the cornea: effects of cross-linking, stromal fibroblasts and cytokine treatment," presented at British Society for Matrix Biology annual Meeting, Cardiff, UK, Sep. 8-9, 2008 (17 pages).
Muller L., et al., "The Specific Architecture of the Anterior Stroma Accounts for Maintenance of Corneal Curvature," Br. J. Opthalmol., vol. 85, pp. 437-443; Apr. 2001 (8 pages).
Mulroy L., et al., "Photochemical Keratodesmos for repair of Lamellar corneal Incisions;" Investigative Ophthalmology & Visual Science, vol. 41, No. 11, pp. 3335-3340; Oct. 2000 (6 pages).
Naoumidi T., et al., "Two-Year Follow-up of Conductive Keratoplasty for the Treatment of Hyperopic Astigmatism," J. Cataract Refract. Surg., vol. 32(5), pp. 732-741; May 2006 (10 pages).
O'Neil A.C., et al., "Microvascular Anastomosis Using a Photochemical Tissue Bonding Technique;" Lasers in Surgery and Medicine, vol. 39, Issue 9, pp. 716-722; Oct. 2007 (7 pages).
Paddock C., Medical News Today: "Metastatic Melanoma PV-10 Trial Results Encouraging Says Drug Company;" Jun. 9, 2009; retrieved from http://www.medicalnewstoday.com/articles/153024.php, on Sep. 26, 2011 (2 pages).
Pallikaris I., et al., "Long-term Results of Conductive Keratoplasty for low to Moderate Hyperopia," J. Cataract Refract. Surg., vol. 31(8), pp. 1520-1529; Aug. 2005 (10 pages).
Pinelli, R. "Corneal Cross-Linking with Riboflavin: Entering a New Era in Ophthalmology." Ophthalmology Times Europe. vol. 2, No. 7, Sep. 1, 2006, [online], [retrieved on May 20, 2013]. Retrieved from the Internet: <URL: http://www.oteurope.com/ophthalmologytimeseurope/Cornea/Corneal-cross-linking-with-riboflavin-entering-a-n/ArticleStandard/Article/detail/368411> (3 pages).
Pinelli R., et al., "C3-Riboflavin Treatments: Where Did We Come From? Where Are We Now?" Cataract & Refractive Surgery Today Europe, Summer 2007, pp. 36-46; Jun. 2007 (10 pages).
Pinelli, R., "Panel Discussion: Epithelium On/Off, Corneal abrasion for CCL contra", presented at the 3° International Congress of Corneal Cross Linking on Dec. 7-8, 2007 in Zurich (36 pages).
Roberto Pinelli et al, "Transepithelial Tensioactive Mediated CXL", Cataract & Refractive Surgery Today Europe, p. 1, URL: http://bmctoday.net/crstodayeurope/pdfs/0409_09.pdf, XP055158069.
Pinelli R., "Resultados de la Sociedad de Cirugia Refractiva Italiana (SICR) utilizando el C3-R" presented at the Istitutor Laser Microchirurgia Oculare in 2007 in Italy (23 pages).
Pinelli et al., "Tensioactive-mediated Transepithelial Corneal Cross-linking—First Laboratory Report", 2009, European Ophthalmic Review, 3(2), pp. 67-70.
Pinelli R., "The Italian Refractive Surgery Society (SICR) results using C3-R" presented Jun. 22-23, 2007 in Italy (13 pages).
Ponce C., et al., "Central and Peripheral Corneal Thickness Measured with Optical Coherence Tomography, Scheimpflug Imaging, and Ultrasound Pachymetry in Normal, Keratoconus-suspect and Post-laser in situ Keratomileusis Eyes," J. Cataract Refract. Surgery, vol. 35, No. 6, pp. 1055-1062; Jun. 2009 (8 pages).
Proano C.E., et al., "Photochemical Keratodesmos for Bonding Corneal Incisions;" Investigative Ophthalmology & Visual Science, vol. 45, No. 7, pp. 2177-2181; Jul. 2004 (5 pages).
Randall, J. et al., "The Measurementand Intrepretation of Brillouin Scattering in the Lens of the Eye," The Royal Society, Abstract only, published 2013 [available online at http://rspb.royalsocietypublishing.org/content/214/1197/449.short] (1 page).
Reinstein, D. Z. et al. "Epithelial Thickness Profile as a Method to Evaluate the Effectiveness of Collagen Cross-Linking Treatment After Corneal Ectasis." Journal of Refractive Surgery. vol. 27, No. 5, May 2011 (pp. 356-363). [Abstract only].
Reiss, S. et al., "Non-Invasive, ortsaufgeloeste Bestimmung von Gewebeeigenschaften derAugenlinse, Dichte undProteinkonzentration unter Anwendung der Brillouin-spektroskopie", Klin Monatsbl Augenheilkd, vol. 228, No. 12, pp. 1079-1085, Dec. 13, 2011 (7 pages).

(56) References Cited

OTHER PUBLICATIONS

Reiss, S. et al., "Spatially resolved Brillouin Spectroscopy to determine the rheological properties of the eye lens", Biomedical Optics Express, vol. 2, No. 8, p. 2144, Aug. 1, 2011 (1 page).
Rocha K., et al., "Comparative Study of Riboflavin-UVA Crosslinking and "Flash-linking" Using Surface Wave Elastometry," Journal of Refractive Surgery, vol. 24 Issue 7, pp. S748-S751; Sep. 2008 (4 pages).
Rolandi et al., "Correlation of Collagen-Linked Fluorescence and Tendon Fiber Breaking Time." Gerontology 1991;27:240-243 (4 pages).
RxList: "Definity Drug Description;" The Internet Drug Index, revised Jun. 16, 2008, retrieved from http://www.rxlist.com/definity-drug.htm, on Sep. 26, 2011 (4 pages).
Saleh et al. "Fundamentals of Photonics" 1991, pp. 74-77.
Scarcelli, G. et al., "Brillouin Optical Microscopy for Corneal Biomechanics", Investigative Ophthalmology & Visual Science, Jan. 2012, vol. 53, No. 1, pp. 185-190 (6 pages).
Sheehan M., et al., "Illumination System for Corneal Collagen Crosslinking," Optometry and Vision Science, vol. 88, No. 4, pp. 512-524; Apr. 2011 (13 pages).
Shell, J., "Pharmacokinetics of Topically Applied Ophthalmic Drugs," Survey of Ophthalmology, vol. 26, No. 4, pp. 207-218; Jan.-Feb. 1982 (12 pages).
Sobol E N et al, "Correction of Eye Refraction by Nonablative Laser Action on Thermomechanical Properties of Cornea and Sclera", Quantum Electronics, Turpion Ltd., London, GB, (Oct. 2002), vol. 32, No. 10, ISSN 1063-7818, pp. 909-912, XP001170947 [A] 1.
Song P., Metzler D. "Photochemical Degradation of Flavins—IV. Studies of the Anaerobic Photolysis of Riboflavin." Photochemistry and Photobiology, vol. 6, pp. 691-709, 1967 (21 pages).
Sonoda S., "Gene Transfer to Corneal Epithelium and Keratocytes Mediated by Ultrasound with Microbubbles," Investigative Ophthalmology & Visual Science, vol. 47, No. 2, pp. 558-564; Feb. 2006 (7 pages).
Spoerl E., et al., "Induction of Cross-links in Corneal Tissue," Experimental Eye Research, vol. 66, Issue 1, pp. 97-103; Jan. 1998 (7 pages).
Spoerl E. et al., "Safety of UVA-Riboflavin Cross-Linking of the Cornea," Cornea, vol. 26, No. 4, pp. 385-389; May 2007 (5 pages).
Spoerl E., et al., "Techniques for Stiffening the Cornea," Journal of Refractive Surgery, vol. 15, Issue 6, pp. 711-713; Nov.-Dec. 1999 (4 pages).
Sun, G.J. et al., Abstract for "Properties of 2,3-butanedione and 1-phenyl-1,2-propanedione as new photosensitizers for visible light cured dental resin composites", Polymer 41, pp. 6205-6212, published in 2000 (1 page).
"Tahzib N.G. et al., ""Recurrent intraocular inflamation after implantation of the Artiflex phakic intraocular lens for the correction of high myopia,"" J Cataract Refract Surg, Aug. 2006; 32(8)1388-91, (abstract) [online] [Retrived Mar. 4, 2013] Retrieved from PubMed, PMID: 16863981".
Tessier FJ, et al., "Rigidification of Corneas Treated in vitro with Glyceraldehyde: Characterization of Two Novel Crosslinks and Two Chromophores," Investigative Opthalmology & Visual Science, vol. 43, E-Abstract; 2002 (2 pages).
Thornton, I. et. al., "Biomechancial Effects of Intraocular Pressure Elevation on Optic Berve/Lamina Cribrosa before and after Peripapillary Scleral Collagen Cross-Linking." Invest. Ophthalm,ol. Vis. Sci., Mar. 2009, 50(3): pp. 1227-1233.
Thornton et al (Investigative Ophthalmology and Visual Science, Mar. 2009, vol. 50, No. 3, pp. 1227-1233).
Tomlinson, A. "Tear Film Osmolarity: Determination of a Referent for Dry Eye Diagnosis", Investigative Ophthalmology & Visual Science, Oct. 2006, vol. 47, No. 10, pp. 4309-4315 (7 pages).
Tomlinson et al. (Investigative Opthalmology and Visual Science 2006, 47 (10), 4309, 4315.
Trembly et al., "Microwave Thermal Keratoplasty for Myopia: Keratoscopic Evaluation in Porcine Eyes," Journal of Refractive Surgery, vol. 17, No. 6, pp. 682-688; Nov./Dec. 2001 (8 pages).
"UV-X: Radiation System for Treatment of Keratokonus," PESCHKE Meditrade GmbH; retrieved from http://www.peschkemed.ch/ on Sep. 27, 2011 (date unknown, prior to Sep. 16, 2008) (1 page).
Vasan S., et al., "An agent cleaving glucose-derived protein crosslinks in vitro and in vivo;" Letters to Nature, vol. 382, pp. 275-278; Jul. 18, 1996 (4 pages).
Verzijl et al. Crosslinking by Advanced Glycation End Products Increases the Stiffness of the Collagen Network in Human Articular Cartilage. Arthritis & Rheumatism vol. 46, No. 1, Jan. 2002, pp. 114-123 (10 pages).
Wollensak G., et al., "Biomechanical and Histological Changes After Corneal Crosslinking With and Without Epithelial Debridement," J. Cataract Refract. Surg., vol. 35, Issue 3, pp. 540-546; Mar. 2009 (7 pages).
Wollensak G., et al., "Collagen Crosslinking of Human and Porcine Sclera," J. Cataract Refract. Surg., vol. 30, Issue 3, pp. 689-695; Mar. 2004 (7 pages).

\* cited by examiner

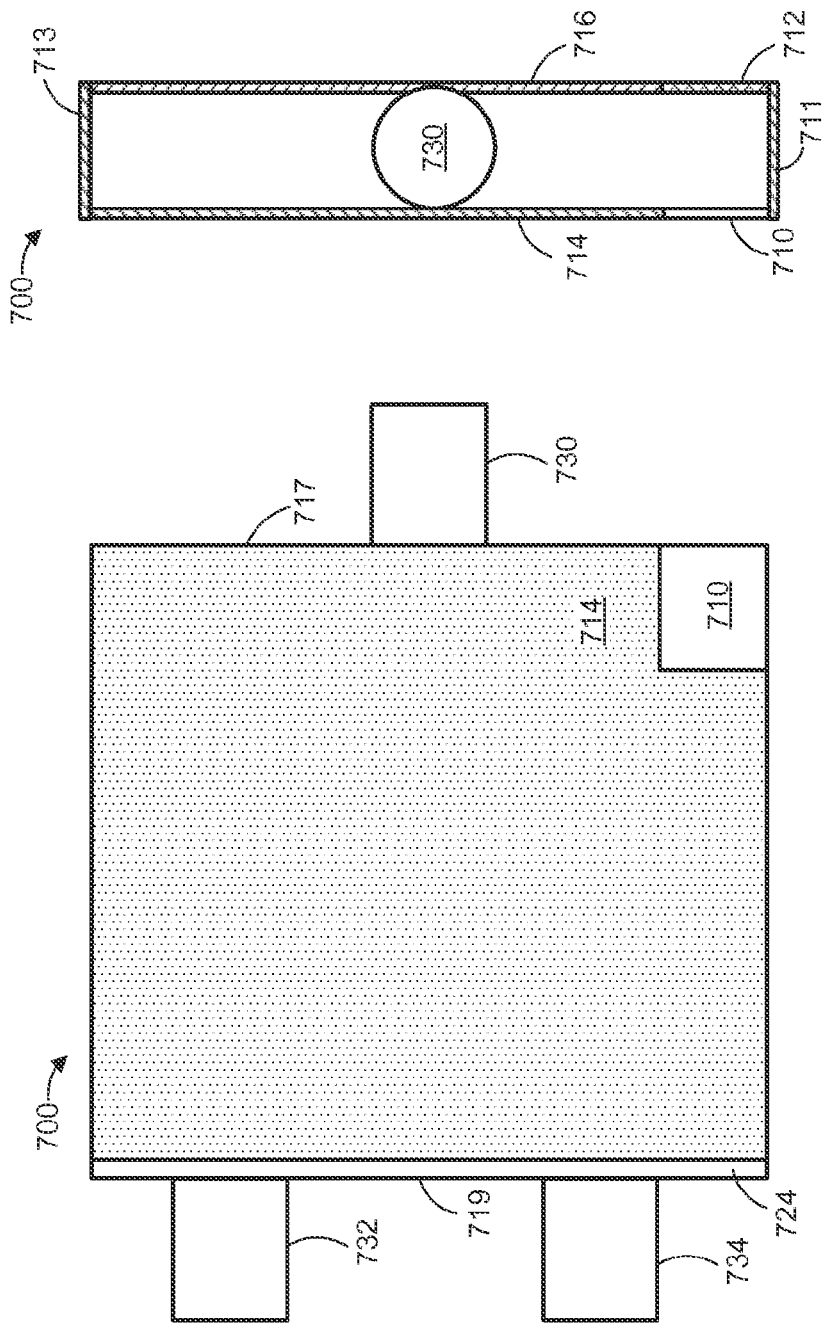

MULTIPASS VIRTUALLY IMAGED PHASED ARRAY ETALON

CROSS REFERENCE TO RELATED APPLICATIONS

This application claims priority to U.S. Provisional Patent Application No. 62/079,544, filed Nov. 13, 2014, the contents of which are incorporated entirely herein by reference.

BACKGROUND

Field of the Invention

Disclosed herein are systems and methods for diagnosing and treating the eye, and more particularly, to systems and methods for determining biomechanical properties of the eye to plan, implement, and/or assess treatments of the eye.

Description of Related Art

Cross-linking treatments may be employed to treat eyes suffering from disorders, such as keratoconus. In particular, keratoconus is a degenerative disorder of the eye in which structural changes within the cornea cause it to weaken and change to an abnormal conical shape. Cross-linking treatments can strengthen and stabilize areas weakened by keratoconus and prevent undesired shape changes.

Cross-linking treatments may also be employed after surgical procedures, such as Laser-Assisted in situ Keratomileusis (LASIK) surgery. For instance, a complication known as post-LASIK ectasia may occur due to the thinning and weakening of the cornea caused by LASIK surgery. In post-LASIK ectasia, the cornea experiences progressive steepening (bulging). Accordingly, cross-linking treatments can strengthen and stabilize the structure of the cornea after LASIK surgery and prevent post-LASIK ectasia.

SUMMARY

Aspects of the present disclosure relate to systems and methods for determining biomechanical properties of the eye to plan, implement, and/or assess treatments of the eye, such as cross-linking treatments. For instance, according to aspects of the present disclosure, systems and methods may employ the principle of Brillouin scattering to determine biomechanical properties of the eye. In particular, the systems and methods may evaluate Brillouin shift to determine viscoelastic and other properties of corneal tissue.

Example embodiments may employ an optical device. The optical device includes a reflective first surface and a partially reflective/transmissible second surface parallel to the first surface. The second surface is spaced from the first surface to define an optical cavity therebetween. The optical cavity has a first end and a second end. The optical device includes an entrance window disposed at the first end of the optical cavity and opposite the second surface. The entrance window is configured to transmit light including light rays into the optical cavity and to allow the light rays to travel to the second surface, causing the light rays to be reflected between the first and second surfaces multiple times and to traverse the optical cavity toward the second end of the optical cavity in a first pass. The optical device includes a first reflective element disposed at the second end of the optical cavity and opposite the second surface. The first reflective element is configured to reflect the light rays to the second surface after the first pass, causing the light rays to be further reflected between the first and second surfaces multiple times and to traverse the optical cavity toward the first end of the optical cavity in a second pass. The light rays travel a first optical path length from the second surface to the first reflective element and back to the second surface. The light rays travel a second optical path length from the second surface to the first surface and back to the second surface during the second pass. The first optical path length is an integer multiple of the second optical path. A portion of light from the light rays is transmitted through the second surface with each reflection at the second surface. The transmitted portions of light generate an interference pattern that provides spectral information for the light.

In other embodiments, the optical device includes a reflective first surface and a partially reflective/transmissible second surface parallel to the first surface. The second surface is spaced from the first surface to define an optical cavity therebetween. The optical cavity has a first end and a second end. The optical device includes an entrance window disposed at the first end of the optical cavity and opposite the second surface. The entrance window is configured to transmit light including light rays into the optical cavity and to allow the light rays to travel to the second surface, causing the light rays to be reflected between the first and second surfaces multiple times and to traverse the optical cavity toward the second end of the optical cavity in a first pass. The optical device includes a first reflective element disposed at the second end of the optical cavity and opposite the second surface. The optical device includes a second reflective element disposed at the first end of the optical cavity and opposite the second surface. The first reflective element and the second reflective element cause the light rays to traverse the optical cavity between the first and second ends in additional passes, the light rays reflecting between the first and second surfaces during each additional pass. The light rays travel a first optical path length from the second surface to the first reflective element and back to the second surface. The light rays travel a second optical path length from the second surface to the first surface and back to the second surface during the second pass. The first optical path length is an integer multiple of the second optical path. The light rays travel a third optical path length from the second surface to the second reflective element and back to the second surface. The light rays travel a fourth optical path length from the second surface to the first surface and back to the second surface during the third pass. The third optical path length is an integer multiple of the fourth optical path. A portion of light from the light rays is transmitted through the second surface with each reflection at the second surface. The transmitted portions of light generating an interference pattern that provides spectral information for the light.

According to aspects of the present disclosure, a system that determines biomechanical properties of corneal tissue includes a light source configured to provide an incident light. The system includes a confocal microscopy system configured to scan the incident light across a plurality of cross-sections of the corneal tissue. The incident light is reflected by the plurality of cross-sections of corneal tissue as scattered light. The system includes a spectrometer configured to receive the scattered light and provide spectral information for the received scattered light. The system includes one or more processors configured to determine a Brillouin frequency shift from the spectral information and to generate a three-dimensional profile of the corneal tissue according to the determined Brillouin frequency shift, The three-dimensional profile provides an indicator of one or more biomechanical properties of the corneal tissue. The spectrometer includes an optical device including a reflective first surface and a partially reflective/transmissible second surface parallel to the first surface. The second surface is spaced from the first surface to define an optical cavity therebetween. The optical cavity has a first end and a second end. The optical device includes an entrance window disposed at the first end of the optical cavity and opposite the second surface. The entrance window is configured to transmit the scattered light including light rays into the optical cavity and to allow the light rays to travel to the second surface, causing the light rays to be reflected between the first and second surfaces multiple times and to traverse the optical cavity toward the second end of the optical cavity in a first pass. The optical device includes a first reflective element disposed at the second end of the optical cavity and opposite the second surface. The first reflective element is configured to reflect the light rays to the second surface after the first pass, causing the light rays to be further reflected between the first and second surfaces multiple times and to traverse the optical cavity toward the first end of the optical cavity in a second pass. The light rays travel a first optical path length from the second surface to the first reflective element and back to the second surface. The light rays travel a second optical path length from the second surface to the first surface and back to the second surface during the second pass. The first optical path length is an integer multiple of the second optical path. A portion of light from the light rays is transmitted through the second surface with each reflection at the second surface. The transmitted portions of light generating an interference pattern that provides the spectral information for the scattered light. The spectrometer also includes a camera configured to detect the interference pattern from the optical device.

Additional aspects will be apparent to those of ordinary skill in the art in view of the detailed description of various embodiments, which is made with reference to the drawings, a brief description of which is provided below.

BRIEF DESCRIPTION OF THE DRAWINGS

FIGS. 7A and 7B are views of a schematic diagram of an example etalon having mounting pins attached thereto.

Figure 1:
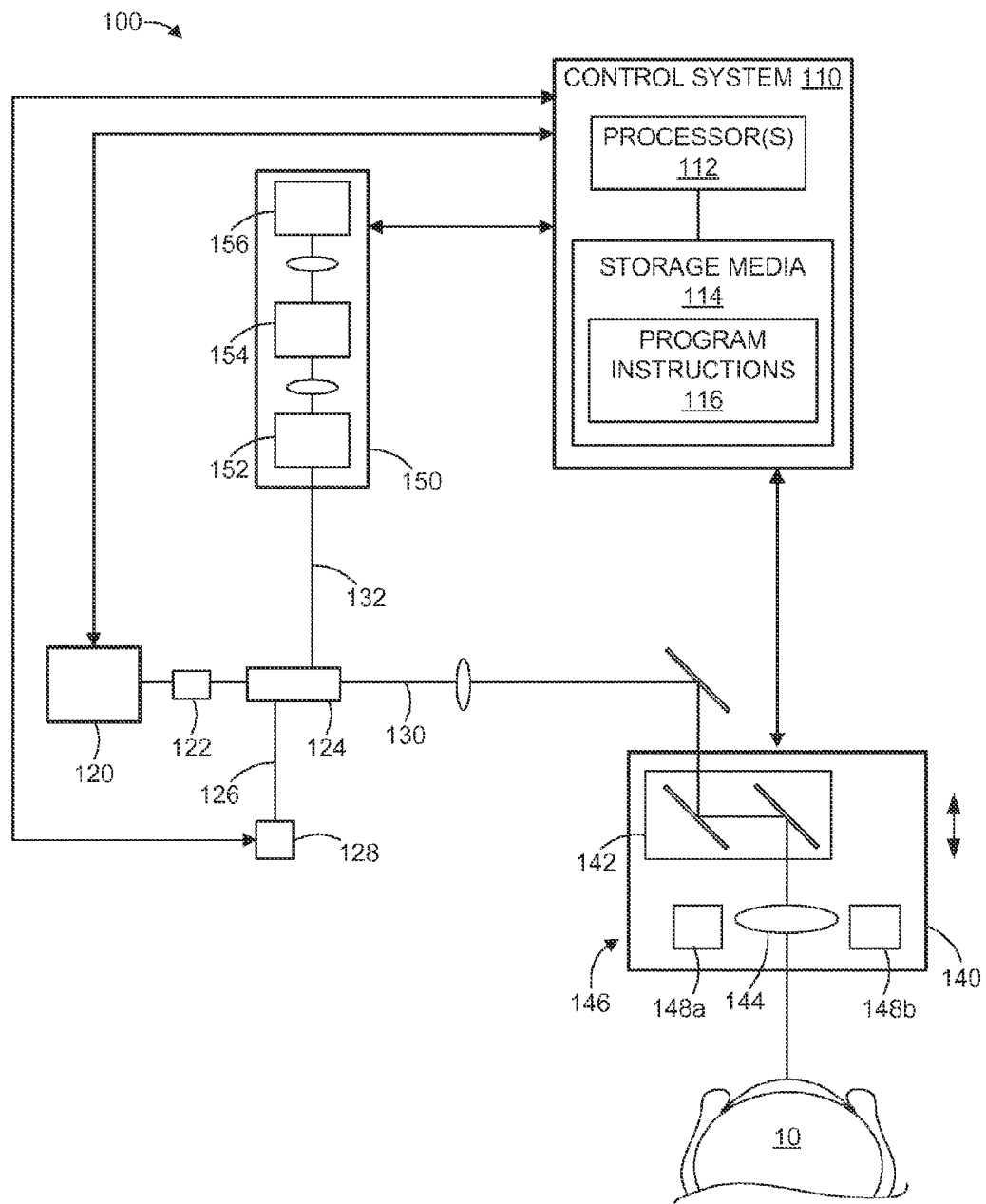
FIG. 1 is a schematic diagram of an example system for measuring biomechanical properties of the eye to plan, implement, and assess treatments of the eye according to some aspects.

While the disclosure is susceptible to various modifications and alternative forms, a specific embodiment thereof has been shown by way of example in the drawings and will herein be described in detail. It should be understood, however, that it is not intended to limit the invention to the particular forms disclosed, but on the contrary, the intention is to cover all modifications, equivalents, and alternatives falling within the spirit of the invention.

DETAILED DESCRIPTION

Aspects of the present disclosure relate to systems and methods for determining biomechanical properties of the eye to plan, implement, and/or assess treatments of the eye. According to some aspects, the systems and methods provide an approach to developing and implementing a plan for treating an eye disorder. For example, the systems and methods can be employed to accurately determine areas of corneal weakness so that cross-linking treatment can be applied to the most appropriate areas.

According to aspects of the present disclosure, systems and methods employ the principle of Brillouin scattering to determine biomechanical properties of the eye. Brillouin scattering involves the inelastic scattering of incident light (photons) by thermally generated acoustic vibrations (phonons). Thermal motions of atoms in a material (e.g., solid, liquid) create acoustic vibrations, which lead to density variations and scattering of the incident light. The scattering is inelastic, which means that the kinetic energy of the incident light is not conserved. The photon either loses energy to create a phonon (Stokes) or gains energy by absorbing a phonon (Anti-Stokes). The frequency and path of the scattered light differ from those of the incident light. The frequency shift, known as the Brillouin shift, is equal to the frequency of the scattering acoustic vibration and provides information regarding the properties of the material. In particular, the systems and methods described herein evaluate the Brillouin shift to measure the biomechanical, e.g., viscoelastic, properties of corneal tissue.

Accordingly, FIG. 1 illustrates an example Brillouin spectroscopy system 100 for determining biomechanical properties of an eye 10 via Brillouin scattering. As shown in FIG. 1, the system employs confocal scanning microscopy (CSM). A light source 120 provides incident light for generating Brillouin scattering in an eye 10. The light source 120 may provide a laser with an ultraviolet (UV), visible, or near infrared (NIR) wavelength, depending on the resolution required. In an example embodiment, the light source 120 includes a narrowband line width diode laser source (approximately 100 kHz-4 MHz) that generates a laser with a NIR wavelength of approximately 780 nm. This wavelength provides an advantageous compromise of spatial and depth resolution while not being too bright for the patient. The light source 120 is coupled to a single mode beam splitting fiber coupler 124 with a specific input/output power ratio (e.g., approximately 5-20%) and a narrowband frequency (e.g., approximately 100 kHz to approximately 4 MHz). With this beam splitting fiber coupler 124, a percentage of the light from the light source 120 based on the input/output power ratio (e.g., approximately 5-20%) passes to a CSM fiber 130 that is coupled to a CSM head 140, while the rest of the light (e.g., approximately 80-95%) passes to a beam dump fiber 126 which is measured with a photodiode 128. It is understood that different input/power ratios may be employed. In addition, although the example of FIG. 1 employs the beam splitting fiber coupler 124, other embodiments can split the light from the light source 120 using any combination of optical devices, such as a beam splitter, a half wave plate/polarizing beam splitter/quarter wave plate combination, etc.

The CSM head 140 includes a set of scanning galvo mirrors 142 and a confocal imaging lens 144. In some embodiments, to achieve a consistent flat field, the confocal imaging lens 144 may be an F-theta lens which may have a focal length on the order of approximately 1 cm to approximately 20 cm. In general, however, the system 100 employs a confocal imaging lens 144 with an appropriate focal length to provide a suitable working distance to the eye 1. The light passing through the fiber 130 is collimated and directed through the set of scanning galvo mirrors 142 where it is then collimated to a spot on the eye 10 via the confocal imaging lens 144. The set of scanning galvo mirrors 142 is used in combination with the confocal imaging lens 144 to scan multiple points of the cornea in enface X-Y slices. For example, a first enface X-Y scan of a specified number of points in a specified pattern is made in a plane starting at the apex of the cornea. The CSM head 140 is then stepped a known distance in the Z-direction (toward the eye 10) to create a second additional enface X-Y scan of the cornea. Subsequently, the CSM head 140 is iteratively stepped in the Z-direction to create additional (e.g., third, fourth, etc.) enface X-Y scans of the cornea for the full thickness of the cornea out to a user specified diameter. Specific regions of interest may be specified for the scanning based on corneal tomography images or other corneal analysis.

It should be understood that the scanning pattern is not restricted to strictly enface imaging. For example, the system can first scan in the z dimension and then step in X-Y dimensions or some other raster scan pattern. Additionally, for example, the first enface X-Y scan can be made in a plane starting at a user defined diameter and then stepped toward the apex of the cornea.

The incident light from the light source 100 experiences scattering when it interacts with the eye 10, i.e., corneal tissue. The light scattered back from the spot of incident light on the eye 10 is directed back through the confocal imaging lens 144 and the set of galvo mirrors 142 and into the beam splitting fiber coupler 124 where the fiber core acts like a pinhole in a confocal scanning microscope. The scattered light is then transmitted back through the beam splitting fiber coupler 124 where approximately 80-95% of the scattered light is directed in a spectrometer single mode fiber 132, while the rest of the scattered light (approximately 5-20%) heads to the laser 120. The laser is equipped with an optical isolator 122 so that the scattered light from the eye 10 does not create feedback within the laser resonator causing potential laser instability.

The spectrometer input fiber 132 extends to a spectrometer system 150 and may have any length to separate spectrometer system 150 practically from other aspects of the system 10, e.g., the light source 120, the CSM head 140, etc. The spectrometer system 150 includes a tilted virtual imaged phased array (VIPA) 154 of a known thickness and free spectral range. The VIPA 154 receives the scattered light from spectrometer input fiber 132 via a lens or lens system.

As described above, the incident light from the light source 120 experiences scattering when it interacts with the corneal tissue. This scattering includes Brillouin scattering and the resulting Brillouin shift can be analyzed to determine biomechanical, e.g., viscoelastic, properties of the corneal tissue. The scattering, however, also includes the additional phenomenon of Rayleigh scattering, which involves elastic scattering of the incident light. This elastically scattered light has the same frequency as the incident light. In addition, the elastically scattered light is orders of magnitude more intense than the Brillouin-scattered light, and the frequency shift between the scatter fractions is very low, e.g., only a few GHz. As such, Brillouin spectroscopy requires separating the Brillouin-scattered light frequencies from the Rayleigh-scattered light frequency.

The system 100 employs the VIPA 154 to separate the Brillouin-scattered light frequencies (Stokes and Anti-Stokes) from the Rayleigh-scattered light frequency. After separation, the light exits the VIPA 154 where it is collected and collimated with a lens or lens system and imaged onto a line scan camera 156 (properly filling the pixels of the line scan camera 156). The pixels of the line scan camera 156 are calibrated for a specific frequency shift per pixel (e.g., 0.15 GHz/px). In this way, the line scan camera 156 acts like a ruler that measures the changing shifts of the Brillouin frequencies with respect to the Rayleigh frequency of the cornea. The line scan camera 156 can be calibrated by measuring standards with known Brillouin frequency shifts. The line scan camera 156 has a given pixel array dimension typically with 512, 1024, or 2048 pixels that is very sensitive to the wavelength of the illumination to allow for short integration times. Therefore, the line scan camera 156 may provide specific methods for increasing sensitivity such as cooling, increased pixel size, etc.

The shift in frequency measured by the line scan camera 156 between the Brillouin frequencies (Stokes and Anti-Stokes) and the Rayleigh frequency is a measure of the bulk modulus or stiffness properties of the cornea of the eye 10. Thus, with the Brillouin spectroscopy system 100, a mapping of the biomechanical properties of the cornea can be made. Mappings can be conducted and compared for normal, diseased, and treated (e.g., cross-linking treated) corneas as well as a quantitative measure of anterior segment anatomy.

A specific approach for increasing sensitivity and shortening exposure times to allow for increased data acquisition rates involves either blocking or attenuating the Rayleigh peak. This allows the highest gain on the line scan camera 156 to be utilized without saturation. One example approach for blocking the Rayleigh peak involves employing a Rubidium vapor cell in-line with the optical system. As shown in FIG. 1, for example, the scattered light from the spectrometer input fiber 132 passes through a Rubidium vapor cell 152, which is tuned to block the Rayleigh frequency. In particular, the Rubidium vapor cell 152 is tuned to the Rayleigh frequency with a known amount of absorption to match the amplitude of the Brillouin frequencies. As such, the Rubidium vapor cell tuned to the Rayleigh frequency acts as a narrowband notch filter, eliminating (or at least reducing) this peak from the spectrum hitting the line scan camera 156. Advantageously, the Rubidium vapor cell 152 removes noise and improves signal-to-noise ratio of the Brillouin peak. The Brillouin frequency shift is then measured by taking the frequency difference between the Stokes and Anti-stokes Brillouin peaks and dividing by two.

Another example approach for blocking the Rayleigh peak involves placing a narrow physical obscuration over the line scan camera pixels associated with the Rayleigh peak. Again, the Brillouin frequency shift described above is measured by taking the frequency difference between the Stokes and Anti-stokes Brillouin peaks and dividing by two.

The ratio of the Rayleigh peak to the Brillouin peak is called the Landau-Placzek Ratio and is a measure of the turbidity of the tissue. Therefore, by tuning the Rubidium absorption filter to absorb a predicted amount of the Rayleigh frequency or using a partially reflective/transmitting obscuration, a quantitative measure of the turbidity of the cornea can be made. This is essentially a densitometry measure of the cornea. The densitometry of the cornea in conjunction with the biomechanical properties of the cornea gleaned from the Brillouin frequency shift may give an enhanced measure of corneal disease states as well as a better measure of the amount of corneal cross-linking imparted to the cornea.

In the example system 100 illustrated and described above with respect to FIG. 1, the spectrometer 150 measures the scattered light received from the CSM head 140 with a VIPA 154 and a line scan camera 156, which may, for instance, employ an electron multiplying charge-coupled device (EM-CCD) camera. The EMCCD camera is a highly sensitive sensor that is well suited for Brillouin imaging.

The embodiments above propose various configurations for a spectrometer system for separating the frequencies of light scattered by an into the Brillouin, Rayleigh, and Raman peaks. It is understood that aspects of the present disclosure may employ a spectrometer system that uses any appropriate technique. In particular, the spectrometer system may use a VIPA in combination with a line scan camera with either physical or narrow bandwidth filters. These images may then be reconstructed to achieve the three dimensional mapping as described further above.

Accordingly, aspects of the present disclosure employ the confocal scanning microscopy system 140 and a spectrometer system 150 to measure the frequency differences between Brillouin-scattered light and the Rayleigh-scattered light. In the case of the cornea, the Brillouin shift is on the order of approximately 2 GHz to approximately 10 GHz. As described above, Brillouin spectroscopy systems and methods can be employed to determine accurately areas of corneal weakness so that cross-linking treatment can be applied to the most appropriate areas. Such systems and methods may also be used during and/or after the cross-linking treatment for real-time monitoring of the cross-linking activity as well as healing processes over time. Through the scanning process, a real-time image of the cornea can be constructed allowing for anatomical measurements of various tissues such as tear film, epithelium, stroma, etc.

During the scanning process, the patient's head may be stabilized through the use of a head and chin rest system (not shown) typically used for many ophthalmic diagnostic and therapeutic devices. The head and chin rest system holds the patient's head and eye socket relatively still. The patient's eye, however, can still move within the eye socket. To address such movement of the eye 10, the system 100 may employ a stereo range finding (SRF) module 146 that includes a pair (or pairs) of cameras 148a-b separated by a known distance viewing the same field of view. As the spot of incident light moves across the cornea, the scanning pattern is seen by the cameras. The disparity between the images from the cameras 148a-b and the expected position based on scanning parameters is a measure of the X-Y-Z position of the particular X-Y scan (defined as the X-Y-Z composite scan). The X-Y-Z composite scan can then be placed in a series of predetermined three dimensional bins (or voxels) for the cornea. The system captures data until enough X-Y-Z composite scans have filled all the bins. These bins are then averaged and the composite corneal mapping of the Brillouin frequency shifts is used to calculate the viscoelastic mapping and other quantitative measures of the cornea. As such, the system 100 continues to scan until all the data is collected, automatically stopping only when all the bins have been filled. In general, the bins represent different three-dimensional sections of the cornea and measurements for each section are associated with the respective bin. Any number of measurements (0, 1, 2, 3, etc.) can be recorded for each bin as desired and the bins can have the same or different numbers of measurements. In addition, the sizes of the bins can vary from very course (e.g., 1 mm×1 mm×100 µm) to very fine (e.g., 25 µm×25 µm×25 µm) depending on requirements for analysis. For example, routine examination of a healthy eye may permit the use of more coarsely sized bins, which typically means that there are fewer bins and less time is required to obtain measurements. The bins can be defined across any area of the cornea, e.g., approximately 9.5 mm to 14 mm across the cornea extending to the sclera.

Accounting for the various amounts of motion of the eye 10 allows the patient to be positioned and the eye 10 to be scanned in a single measurement period. This approach reduces, if not eliminates, the number of repeat measurements requiring repositioning of the patient, in contrast to other diagnostic systems such as corneal tomography systems which often require the patient to be repositioned several times to obtain a quality image.

It should be understood that, according to additional and/or alternative aspects of the present disclosure, the corneal tomography can be measured by other systems. For example, an alternative to utilizing the scanned beam is to project a static grid at a different wavelength to determine the three dimensional volume of the cornea using the same stereo pair cameras.

Mapping of the Brillouin shifts gives a biomechanical mapping of the viscoelastic properties of the tissue. The mapping of the Brillouin shifts may be registered using the pair of cameras 148a-b which allows for three dimensional registration of the points as they are taken, especially in the case where the data acquisition is slow. In this manner, eye movement taken into account.

Raman scattering is another phenomenon involving inelastic scattering processes of light with vibrational properties of matter. The detected frequency shift range and type of information extracted from the sample, however, are different. Brillouin scattering denominates the scattering of photons from low-frequency phonons, while for Raman scattering, photons are scattered by interaction with vibrational and rotational transitions in single molecules. Therefore, Brillouin scattering and Raman scattering provide different information about the sample. Raman spectroscopy is used to determine the chemical composition and molecular structure, while Brillouin scattering measures properties on a larger scale, such as the elastic behavior.

A problem is presented, however, in that the biomechanical data and the corneal tomography data may not be directly correlated. For example, the biomechanical data derived from the measured Brillouin scattering frequencies and the corneal tomography data derived from the captured stereographic images may be captured at different points in time or over different durations. Because the patient's eye may move during the measurement procedures, the position and/or orientation of a map of the biomechanical data may differ from that of the corneal tomography data. Additionally, for example, while the biomechanical data is derived from a confocal system that scans point by point over successive X-Y planes stepped in a Z direction, the corneal tomography data can be derived from one or more stereographic images captured over one or more areas of the cornea.

The system 100 may operate in accordance with instructions from a control system 110 that includes one or more processor(s) 112 and data storage 114. The data storage 114 may include program instructions 116 that can be executed by the processor(s) 112 to cause the control system 110 to carry out one or more operations. In particular, when the processor(s) execute the program instructions 116, the system 100 may function as described herein and in connection with the process 200 described in connection with FIG. 2.

In the systems and methods described herein, a clock is maintained (e.g., via the processor(s) 112 in the control system 110) so that all measurements for the biomechanical data and the corneal tomography data are made at known times. Additionally, the iris image capture systems can obtain iris image data at all known times for which the biomechanical data and the corneal tomography data is measured. Because the iris has distinct anatomical features, the iris image data provides an indication of the orientation of the eye 10 (and, thus, the corneal tissue) at each point in time. Accordingly, the iris image data at each known point in time is utilized to provide a common frame of reference against which the biomechanical data and corneal tomography data can be translated. In other words, the biomechanical data and the corneal tomography data can be aligned against the iris image data to determine a set of 3D voxel data representing at least the biomechanical data, corneal tomography data, and iris image data for the eye 10. The 3D voxel data thus correlates the measured biomechanical data, corneal tomography data, and iris image data.

The 3D voxel data can be processed (e.g., via the control system 110) to determine a treatment plan for correcting a condition of the eye 10. As one non-limiting example, a finite element analysis can be employed to create the treatment plan. Such a treatment plan can provide a new detailed analysis of how the viscoelastic properties (or other biomechanical properties) of the eye 10 may correspond to the anatomical features indicated by the corneal tomography. As such, a more informed and effective treatment plan or eye condition assessment can be developed by the systems and methods of the present disclosure.

According to some aspects of the present disclosure, 3D voxel data can be determined prior to any eye treatment therapy being applied to the eye 10. In such instances, the 3D voxel data can be utilized to diagnose particular eye conditions of the eye 10. Additionally, in such instances, the 3D voxel data can be utilized to determine the treatment plan as described above.

According to additional and/or alternative aspects, the 3D voxel data can be determined during an eye therapy procedure. For example, the 3D voxel data can be utilized to monitor iterative changes to the biomechanical and/or tomographic properties of the eye 10 as the eye therapy is being applied. In some instances, the 3D voxel data can be used as feedback to iteratively determine and/or adjust a treatment plan based on an analysis of the 3D voxel data. In other words, the systems 100 described and illustrated herein can be employed as a feedback system to iteratively and/or continuously control aspects of the eye therapy being applied to the eye 10.

According to further aspects of the present disclosure, the treatment plan can be programmed into an eye treatment system to correct a condition of the eye 10. For example, the eye treatment system can include a cross-linking system, a LASIK system, combinations thereof, and/or the like. The eye treatment system includes an eye tracking system that is configured to monitor the patient's iris.

Advantageously, because the treatment plan data is based on the 3D voxel data and thus the iris image data, the eye treatment system can be automatically aligned to the treatment plan data based on the real-time monitoring of the patient's iris by the eye treatment system. That is, the real-time imagery obtained by the eye treatment system can be aligned with the iris image data of the treatment plan to automatically match patterned eye treatment therapies applied by the eye treatment system to the patient's cornea. For example, the patterns of photoactivating light applied by the PIXL system to the cornea to initiate cross-linking of the corneal fibers can be automatically determined, oriented, and aligned with the patient's cornea based on the real-time monitoring of the patient's eye and the treatment plan data. As shown in FIG. 1, the control system 110 may provide 3D voxel data to a treatment system, for example, a cross-linking treatment system that determines a desired pattern of cross-linking activity for the cornea and applies photoactivating light accurately according to the pattern.

Figure 2:
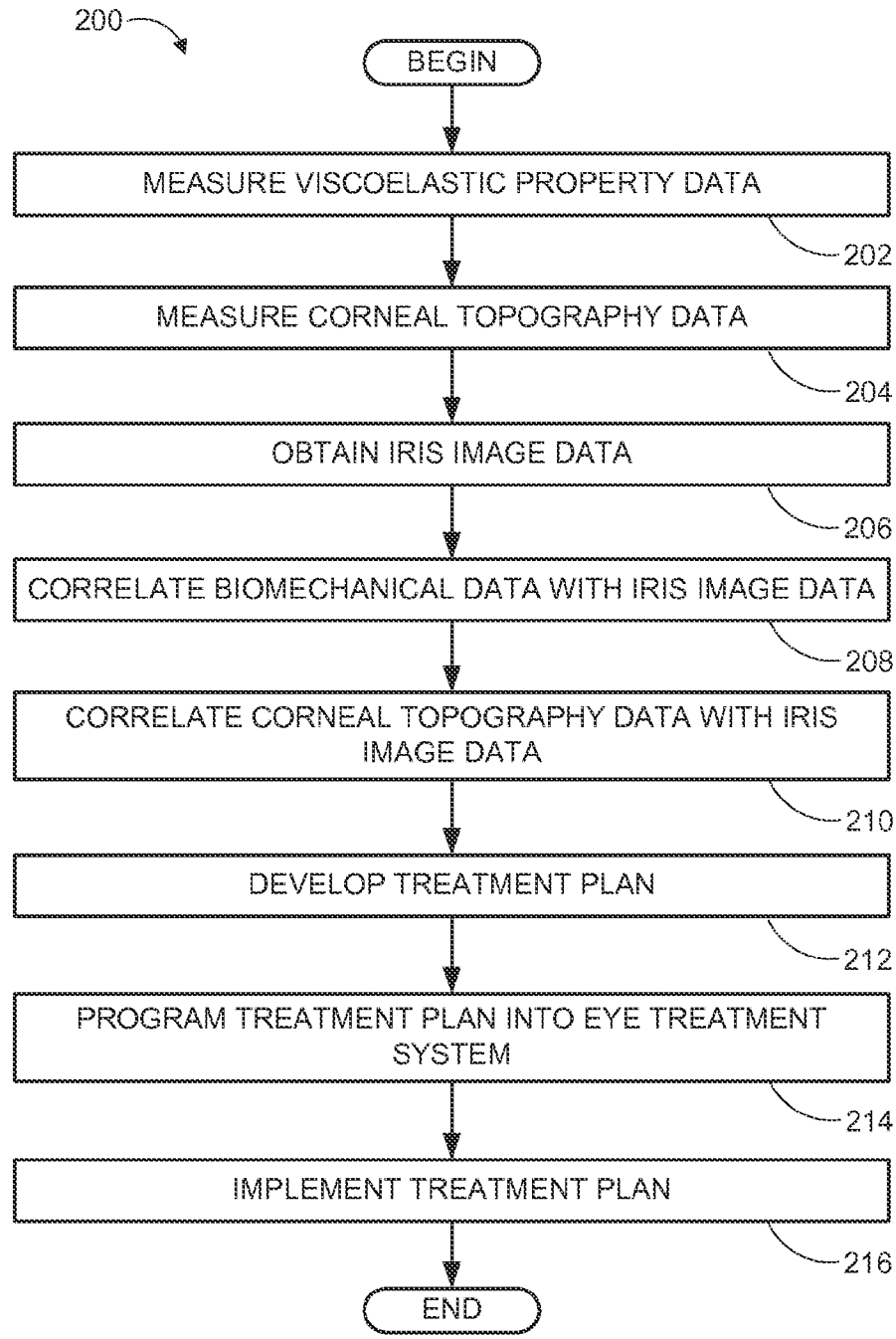
FIG. 2 is a flowchart of an example process for operating an eye treatment system.

Referring now to FIG. 2, a flow chart for an example process 200 for measuring biomechanical properties of the eye to plan, implement, and assess treatments of the eye 10 is illustrated according to some aspects of the present disclosure. At step 202, the biomechanical data is measured for a cornea. As described above, the biomechanical data can be measured by a CSM head (e.g., the CSM head 140) and a spectrometer (e.g., the spectrometer 150). The clock provided by the control system 110 determines time data (i.e., time stamp data) such that each biomechanical data point measured is associated with a known measurement time. The biomechanical data and the associated time data can be stored in a memory.

At step 204, the corneal tomography data is measured for the cornea. As described above, the corneal tomography data is measured by the plurality of stereoscopic cameras 148a-b at known measurement time(s). The corneal tomography data and the associated time data can be stored in the memory.

At step 206, the iris image data is obtained for all known times at which the biomechanical data is measured and all known times at which the corneal tomography data is measured. As described above, the iris image data can be obtained by the image capture device 146 having a field of view configured to be aligned with the eye 10. The iris image data and the associated time data can be stored in the memory.

At step 208, each point of biomechanical data is correlated with the iris image data that was captured at the same time that the biomechanical data was measured. Thus, each point of biomechanical data can be correlated with the respective iris image data that was obtained at the measurement time associated with that point of biomechanical data.

At step 210, the corneal tomography data is correlated with the iris image data that was captured at the same time that the corneal tomography data was measured. This can be achieved by correlating the tomography data to the iris image data based on the time data associated with each data set.

Accordingly, after step 208 and step 210, the biomechanical data and the corneal tomography data can be cross-referenced against a common frame of reference provided by the iris image data associated with both the biomechanical data and the corneal tomography data. At step 212, the 3D voxel data is generated by correlating the biomechanical data with the corneal tomography data based on the respectively associated iris image data. The 3D voxel data thus provides a three dimensional mapping of the biomechanical data, the corneal tomography data, and the iris image data.

At step 212, the 3D voxel data can be utilized to develop a treatment plan. The treatment plan is thus, in part, based on the iris image data, which can be subsequently utilized during an eye therapy procedure to ensure that the treatment plan is precisely applied to the eye 10 despite movement of the eye 10.

At step 214, the treatment plan is programmed into an eye treatment system. At step 216, the eye treatment system applies an eye therapy according to the treatment plan. For example, the eye treatment system can include a cross-linking system, a LASIK system, combinations thereof, and/or the like. The eye treatment system includes an eye tracking system that is configured to monitor the patient's iris. As described above, the application of the eye therapy can include tracking the iris to automatically apply the eye therapy in proper orientation and alignment with the treatment plan (based on the iris image data aspects of the 3D voxel data underlying the treatment plan).

FIG. 2, described by way of example above, represents one algorithm that corresponds to at least some instructions executed by the control system 110 (e.g., by the processor(s) 112 executing program instructions 116) to perform the above described functions associated with the described concepts. It is also within the scope and spirit of the present concepts to omit steps, include additional steps, and/or modify the order of steps presented above. Additionally, it is contemplated that one or more of the steps presented above can be performed simultaneously.

It is contemplated that the feedback provided by the systems and methods of the present disclosure can be utilized to determine when milestones are achieved during an eye therapy procedure. For example, during a cross-linking procedure, a first pattern of photoactivating light can be applied until the control system 110 determines that the 3D voxel data is indicative of a first shape change (i.e., a first milestone), then a second pattern can be applied until the control system 110 determines that the 3D voxel data is indicative of a second shape change, and so on. It should be understand that other eye therapy procedure parameters can be similarly controlled based on the 3D voxel data determined and processed as feedback by the systems and methods of the present disclosure.

According to other additional and/or alternative aspects, the 3D voxel data can be determined after an eye therapy procedure. For example, the 3D voxel data can be utilized to verify whether the eye therapy achieved the intended result. As another example, the 3D voxel data can be utilized to comparatively analyze the post-operative conditions of the eye 10 relative to the pre-operative conditions. Additionally, for example, the 3D voxel data can be utilized to monitor the conditions of the eye 10 to ensure that the changes effected by the eye therapy are stable. In particular, the 3D voxel data can be determined and analyzed after a cross-linking eye therapy procedure to confirm that the strengthening of the corneal tissue is stable and/or identify potential issues with the stability of the corneal tissue strengthening.

While the process 200 is described and illustrated with respect to iris imaging and iris image data, it should be understood that the process 200 can additionally and/or alternatively include the other types of registration imaging and resulting registration data described above. Accordingly, the registration aspects of the systems 100 and process 200 can include imaging of one or more anatomical features (e.g., one or more iris textures, scleral arteries, scleral veins, retinal arteries, retinal veins, limbus boundary, scleral boundary, etc.) and/or one or more external information (e.g., structured light) according to some aspects of the present disclosure.

As noted in connection with FIG. 1, the spectrometer system 150 includes a VIPA 154, which is used to generate an interference pattern that angularly separates the intensity of incoming light according to wavelength. The VIPA 154 is a pair of parallel reflective surfaces, which create an optical cavity between the two. One of the reflective surfaces is at least partially transmissible such that each reflection from the partially transmissible surface allows a small amount of light to pass through. For a given ray of light, each transmission of light through the partially transmissible surface creates a cone of light that corresponds to a virtual image of the previous transmission point, but delayed by an optical path length that is roughly twice the width of the optical cavity. The interference pattern of the resulting array of virtual images, each offset by a constant optical path length has fringes of constructive and destructive interference pattern. Different wavelengths constructively interfere at different angles, and so the interference pattern can be used to identify the spectral content of the light that was incident through the entrance window.

According to some aspects of the present disclosure, a VIPA may be formed by an etalon having two parallel surfaces, one of which is reflective and the other of which is partially reflective/transmissible. However, upon a given ray of light traversing the etalon, rather than dumping any remaining light into a light absorber, the light may be reflected back through the etalon for a second pass through the optical cavity. In particular, light is reflected back through the optical cavity of the etalon such that the next reflection from the partially transmissible surface is offset from the previous one by an integer multiple of the optical path length difference between subsequent reflections by the partially transmissible surface on the original pass through the optical cavity. In addition, the reflected light is directed along an opposite angle to the original incident light. As a result, the reflected light makes a second pass through the etalon with each partial transmission through the partially transmissible surface providing additional virtual images that are offset from the original set of virtual images by an integer of the optical path length.

Accordingly, the disclosed multipass VIPA etalons are capable of providing far more passes through the etalon than typical non-multipass etalons. Because far more passes are possible, reflectivity of the partially transmissible surface may be increased relative to a typical non-multipass etalon. By increasing the reflectivity, and therefore the number of passes through the etalon for a given ray of light, the finesse of the resulting fringe pattern is greatly enhanced, and therefore the sensitivity of the VIPA to changes in wavelength is greatly enhanced. The multipass VIPA etalons disclosed herein are therefore well-suited for application in the spectrometer system 150 described above in connection with FIG. 1.

The etalons described herein may be formed of a substrate of fused silica or glass or another thermally stable material (e.g., poly(methyl methacrylate) (PMMA)). The substrate can also have a substantially uniform index of refraction (e.g., about 1.45). The various reflective surfaces may be formed by applying coatings and/or etching features on the substrate by a variety of techniques (e.g., by sputtering, depositing, electroplating, spin coating, etc.). To achieve a desired degree of reflectivity for a given reflective coating, a surface may be coated with a pattern of reflective material (e.g., a layer of metal such as silver, gold, aluminum, etc.) according to a variety of techniques. In some cases, coatings are applied with a thickness less than about 75 micrometers. The surfaces of the substrate may be polished (or otherwise machined) to achieve high degree of flatness and surface quality, such as a tolerance for no scratches greater than 10 micrometers in width, no digs greater than 5 micrometers in diameter (i.e., s/d<10/5). In addition, the substrate can be formed such that the parallel surfaces (i.e., the reflective and partially transmissible surfaces) are parallel to within 0.02 arcseconds. In some examples, the etalons described herein may include a 0.25 mm chamfer at 45 degrees around all edges to protect the etalon from chipping and improve its resiliency. However, some implementations may not include a chamfer.

Figure 3A:
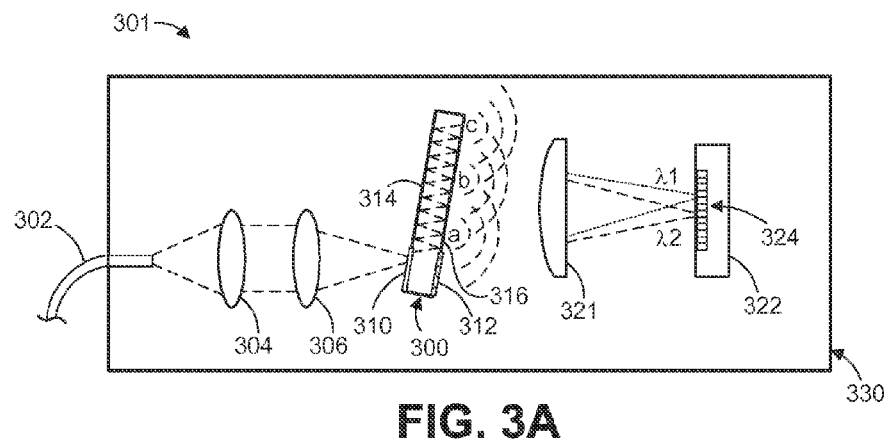
FIG. 3A is a schematic diagram of an example spectrometer that includes an example VIPA formed by an etalon.

FIG. 3A is a schematic diagram of an example spectrometer 301 that includes an example VIPA formed by an etalon 300. The spectrometer 301 includes a housing 330 that does not allow ambient light into the housing 330. A fiber 302 enters through the housing and emits light that is directed to an entrance window 310 of the etalon 300 by collimating lens 304 and focusing lens 306. Some of the light that enters the etalon 300 is reflected multiple times between parallel reflective surfaces resulting in an interference pattern. A Fourier lens 321 is arranged between the etalon 320 and a camera 322. The Fourier lens 321 is aligned to direct the output of the etalon (i.e., the virtual image array interference pattern) to the camera 322 in a wavelength-dependent fringe pattern. The camera 322 includes a light-sensitive array 324 at an imaging plane of the lens 321. The light-sensitive array 324 may be, for example, a pixelated array of light-sensitive elements each configured to generate an electrical signal related to incident light intensity (e.g., a CMOS or CCD array). Each element of the light-sensitive array 324 samples a respective angle of the fringe pattern. Because the fringe pattern separates wavelengths at different angles, the intensity measured at different locations of the light-sensitive array 324 (e.g., at different pixels) indicates the intensity of the incident light at respective wavelengths.

Figure 3B:
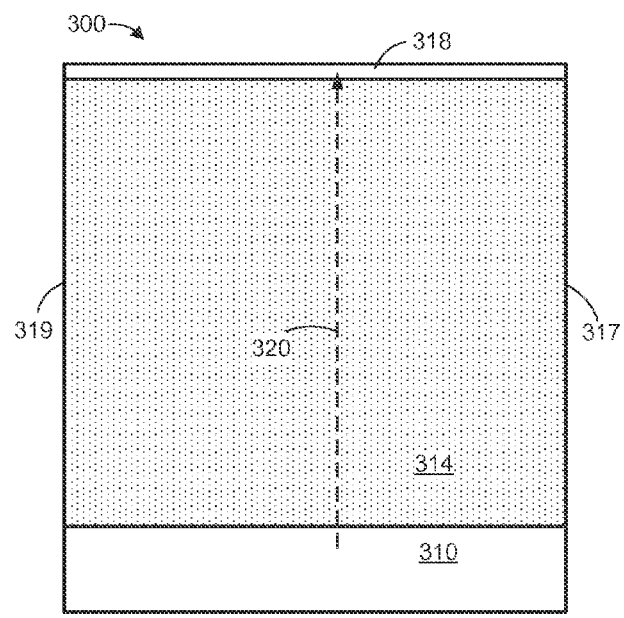
FIGS. 3B and 3C are views of a schematic diagram of the example etalon.
Figure 3C:
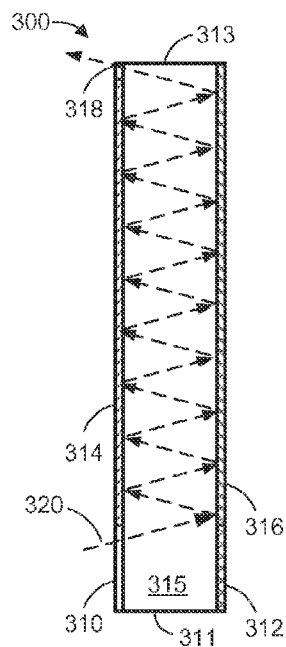

FIGS. 3B and 3C are views of a schematic diagram of the example etalon 300. The etalon 300 is a rectangular cuboid with a width, height, and thickness that extend in respective mutually orthogonal directions. The thickness dimension is bounded by two parallel faces that are rectangles that span the height and width of the etalon 300. The first face of the etalon 300 includes an entrance window 310 a reflective surface 314, and an exit window 318. The second face of the etalon includes a non-transmissible region 312 and a partially transmissible surface 316. The remaining faces of the rectangular cuboid include a top 313 and a bottom 311, which bound the height of the etalon 300, and two sidewalls 317, 319, which bound the width of the etalon 300.

The thickness of the etalon 300 may be about 5 millimeters (mm), and the height and width may each be about 15 mm to about 40 mm (e.g., 25 mm). Various dimensions are possible depending on implementation. However, for an etalon with opposing faces that are parallel surfaces to a high degree of precision (e.g., a relative angle of less than 0.02 arcseconds), the etalon 300 may have a relatively small height/thickness ratio (or width/thickness ratio), such as less than about 10. At such ratios, the degree of precision between the parallel surfaces may be more readily manufactured, and more stable once manufactured. In particular, at such ratios, the etalon 300 may be mounted without exerting significant stress across the width/height of the etalon 300. Such stresses could slightly warp or bend the etalon 300 and bring the opposing faces out of parallel alignment.

To create a rectangular cuboid with parallel opposing faces, a glass substrate may be polished and then coated with a layer(s) of reflective and/or transparent material patterned on different regions so as to provide desired transmission/reflection characteristics. The entrance window 310 is a transparent region of the first face through which incident light enters the etalon 300. The entrance window spans at least a portion of the width of the etalon 300, and a portion of the height of the etalon 300. In some examples, the entrance window 310 may span the entire width of the etalon 300 and may span a portion of the height that terminates at the bottom 311, as shown in FIG. 3B. The entrance window 310 is immediately adjacent to the reflective surface 314 and can be co-planar with the reflective surface 314 because both are formed on the same face of the etalon 300.

The reflective surface 314 can be a portion of the first face that is immediately adjacent to the entrance window 310. The reflective surface 314 can be formed by a coating of metal (e.g., silver, gold, aluminum, etc.) that is layered over the first face of the etalon 300 so as to reflect light from the interior of the etalon 300 back toward the interior. The reflective surface 314 may reflect approximately 100% of light incident from the interior of the etalon 300.

The first face of the etalon 300 also includes the exit window 318, which allows remaining multiply-reflected light that reaches the top 313 to exit the etalon 300. By allowing the light to escape the etalon 300 upon reaching the top 313, the exit window 318 prevents light from being reflected back into the etalon 300, which reflections would be out of phase with the virtual images and thus reduce the finesse of the eventual fringe pattern. As shown in FIG. 3B, the exit window 318 can span the entire width of the etalon 300, and span a portion of the height that terminates at the top 313. Thus, the exit window 318 can be situated along the top 313 of the etalon, and the entrance window 310 can be situated along the bottom 311. As such, a ray of light 320 that enters through the entrance window 310 can be reflected multiple times within the optical cavity 315 between the reflective surface 314 and the partially transmissible surface 316 and then exit the etalon 300 through the exit window 318.

On the second face, the non-transmissible region 312 may be a reflective and/or absorbing surface (e.g., coating) that is located across the thickness of the etalon 300 from the entrance window 310. In some cases, the dimensions of the non-transmissible region 312 may be the same as the dimensions of the entrance window 310 and may be located directly across the thickness of the etalon 300 from the entrance window 310. For instance, the area of the non-transmissible region 312 can be defined by projecting the area of the entrance window 310 through the thickness of the etalon 300 in a direction normal to the first and second faces of the etalon 300. Thus, both the entrance window 10 and the non-transmissible region 312 may span the full width of the etalon 300 and may span the same height that terminates along the bottom 311 of the etalon 300. The entrance window 310 and the non-transmissible region 312 may have a height of about 5 mm, for example.

The partially transmissible surface 316 is also located on the second face of the etalon 300 and is located adjacent to the non-transmissible region. The partially-transmissible surface 316 may span the entire width of the etalon 300 and may span the remaining height of the etalon 300 after subtracting the height of the non-transmissible region 312.

The partially-transmissible surface 316 can be formed by a coating and/or surface treatment applied to the second face of the etalon (e.g., a metallic coating patterned on the second face to provide a desired degree of reflectivity). The partially-transmissible surface 316 may have a reflectivity between about 95% and about 99.98%. Thus, for light incident on the partially transmissible surface 316 a portion is transmitted through, and the rest is reflected back toward the reflective surface 314.

In the drawings a path of a single ray of light 320 is shown propagating through the etalon 300. The ray of light 320 enters the entrance window 310 at a small angle of incidence respect to the entrance window 310. The light 320 propagates through the material of the etalon and is incident on the partially transmissible surface 316. A portion of the original light is then transmitted out of the etalon 300, through the partially transmissible surface 316, and the rest of the light is reflected back toward the reflective surface 314. The angle of incidence of the light 320 may be about 0.5 degrees to about 3 degrees, and may be effected by an arrangement in which the etalon 300 is mounted at angle to an optical axis of the incoming light, as shown in FIG. 3A. The angle of incidence is large enough that the ray 320 reaches the partially transmissible surface 316, rather than the non-transmissible region 312, and the reflected portion reaches the reflective surface 314, rather than exiting back through the entrance window 310. It is further noted that any incident light that instead reaches the non-transmissible region 312 is either absorbed or reflected back out through the entrance window 310, and therefore is not reflected within the optical cavity 315 of the etalon 300. Significantly, the non-transmissible region 312 prevents light from being transmitted through the second face of the etalon 300 if it is not on a ray that will be reflected multiple times within the optical cavity 315 of the etalon 300. As such, the etalon 300 is configured to allow contributions to the light interference pattern that come solely from rays of light that are reflected multiple times within the etalon 300.

After the initial reflection from the reflective surface 314, the ray of light 320 continues to be reflected multiple times within the optical cavity 315 between the partially transmissible surface 316 and the reflective surface 314. Each reflection from the partially transmissible surface 316 results in a portion of the light being transmitted through. In particular, for 100% reflection by the reflective surface 314, the amount of light that is transmitted through the partially transmissible surface 316 at the $n^{th}$ reflection is: $I_0 (1-R)^n$, where $I_0$ is the intensity of the light 320 upon entering the entrance window 310, R is the portion of light that is reflected by the partially transmissible surface on each reflection, and n is the number of reflections.

Thus, the multiply reflected light 320 results in multiple transmission points through the etalon, and each transmission point is delayed with respect to the previous one by a phase delay that corresponds to the optical path length between subsequent reflections from the partially transmissible surface 316. For small angles of reflection, the optical path length between subsequent reflections is approximately twice the thickness of the etalon 300. Moreover, when the two surfaces 314, 316 are parallel surfaces (i.e., the thickness of the etalon 300 is constant throughout the entire path of the multiply reflected light 320), the relative phase delay between each subsequent transmission through the partially transmissible surface 316 remains constant throughout the path of the light 320.

To facilitate understanding, the diagram in FIG. 3A depicts three example transmission cones of phase-delayed light resulting from light transmitted through the etalon 300. The three transmission cones are labeled point a, for a point of transmission close to the bottom 311 of the etalon, point b, for a point of transmission near the middle of the etalon, and point c, for a point of transmission near the top 313 of the etalon. Wave fronts from each of the three transmission points interfere with one another to create an interference pattern that is directed to the camera 322 by the Fourier lens 321. The interference pattern includes regions of constructive and destructive interference. The locations in the pattern for constructive/destructive interference vary with wavelength, and so the intensity of the interference pattern at different wavelengths provides information about the wavelengths of light included in the light 320. In general, the definition of the fringes in the interference pattern (e.g., the finesse) increases with the number of interfering points of transmission through the partially transmissible surface 316. As shown in FIG. 3A, the interference pattern may be focused through the Fourier lens 321 such that constructive interference at a first wavelength $\lambda 1$ is directed to one region of the light-sensitive array 324 and constructive interference at a second wavelength $\lambda 2$ is directed to another region of the light-sensitive array 324. Thus, intensity readings from different pixels of the light-sensitive array 324 can be used to determine the intensity of the incident light at respective wavelengths.

The diagram in FIG. 3A shows three example transmission points a, b, c, but of course some implementations will be configured to provide many more than three points of transmission for a given ray through the etalon 300. For instance, with an angle of internal reflection of about 1 degree, and a thickness of 5 mm, each point transmission on the partially transmissible surface 316 is about 0.17 mm apart (5 mm 2))tan(1°)). Over a height of 20 mm, the ray of light 320 is reflected from the partially transmissible surface 316 about 100 times, and each point of transmission is phase delayed with respect to the previous one by an optical path length of approximately 10 mm. In such an example, if the reflectivity of the partially transmissible surface 316 is 0.95, the remaining intensity of the light after the hundredth reflection is about 0.5% of the original intensity ($0.95^{100}$) and that remaining intensity exits the etalon 300 through the exit window 318. Many other examples are also possible. To provide a target number of reflections within the etalon 300 (and thus separate phase-delayed transmissions through the partially transmissible surface 316), a designer could adjust the height and thickness dimensions of the etalon 300, the reflectivity of the partially transmissible surface 316 and the angle of incidence of light that enters the etalon 300. In some cases, the parameters may be selected such that the intensity of a given ray of light (e.g., the ray 320) has been substantially transmitted through the partially transmissible surface 316 by the time the ray reaches the exit window 318. For instance, the reflectivity may be selected such that the amount of light intensity that exits through the exit window 318 is less than about 1% of the incident light intensity (e.g., $R=0.01^{1/n}$, where n is the total number of reflections from the partially transmissible surface 316).

Finally, the remaining faces of the etalon (i.e., the top 313, bottom 311, and sidewalls 317, 319) can be reflective surfaces that are formed to be orthogonal to the front and back faces. The sidewalls 317, 319 and top/bottom 313, 311 can thus reflect any light that reaches them back into the optical cavity 315 while keeping the light in phase and aligned. The perpendicular faces may not require an optical coating to be applied, because the angle of incidence of any rays of light that would reach them is high enough to ensure total internal reflection, but the faces are desirably smooth and perpendicular to both the reflective surface 314 and partially transmissible surface 316.

Figure 4A:
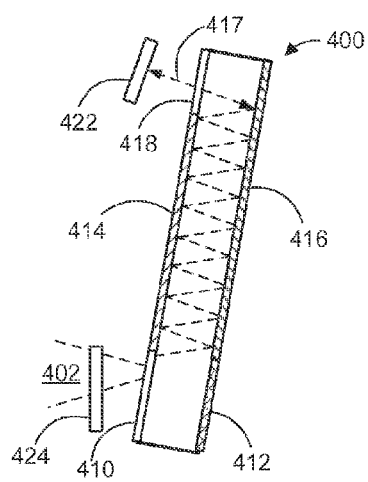
FIGS. 4A and 4B are views of an example VIPA that includes aligned mirrors for directing light to undergo multiple passes through an etalon.
Figure 4B:
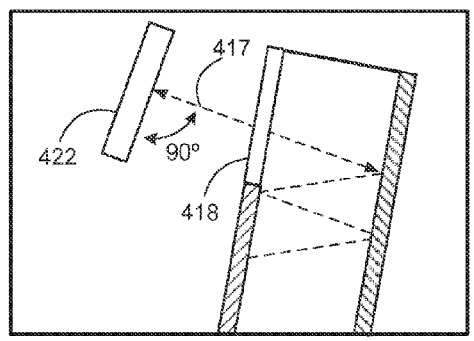
Figure 4C:
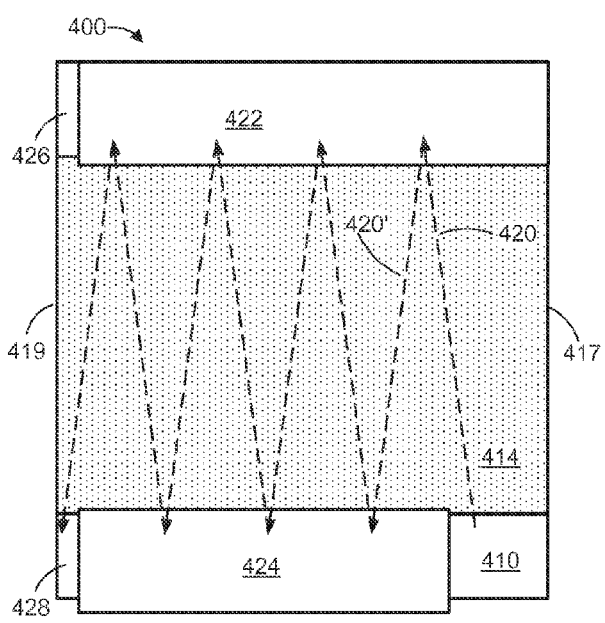
FIGS. 4C and 4D are views of a schematic diagram of the example etalon and aligned mirrors.
Figure 4D:
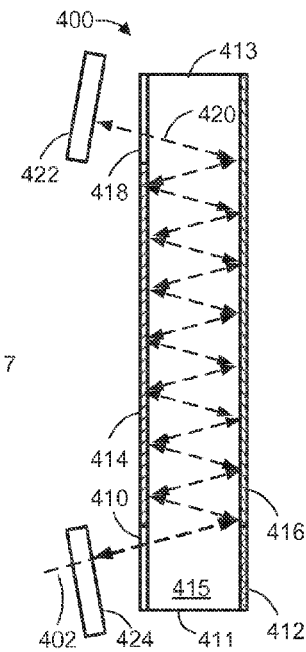
Figure 4E:
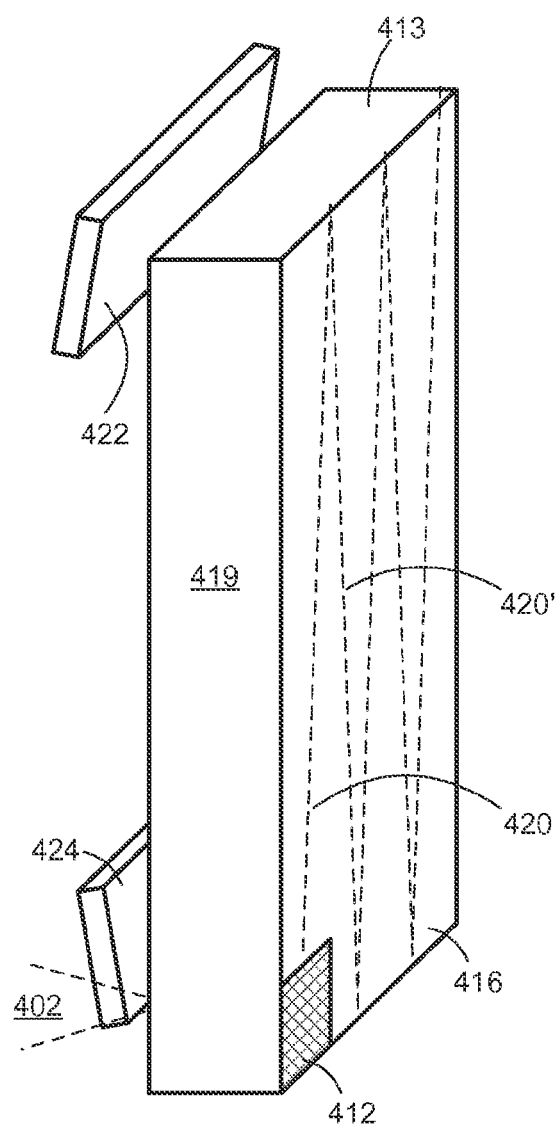
FIG. 4E is an aspect view of the example etalon and aligned mirrors.

FIGS. 4A and 4B are views of an example VIPA that includes aligned mirrors 422, 424 for directing light to undergo multiple passes through an etalon 300. FIGS. 4C and 4D are views of a schematic diagram of the example etalon and aligned mirrors 422, 424. FIG. 4E is an aspect view of the example etalon 400 and aligned mirrors 422, 424. The etalon 400 can be similar in many respects to the etalon 300 of FIG. 3, and corresponding elements are generally labeled with a reference number one-hundred greater than the corresponding feature of the etalon 300, except for that a mirror 422 is situated to reflect light that exits the etalon through the exit window 418 back into the etalon 400 through the exit window 418, and a mirror 424 that is situated to reflect light that exits the etalon through the entrance window 410 back into the etalon 400. The etalon 400 includes a first face and a second face that are aligned parallel with one another. The first face includes an entrance window 410, a reflective surface 414, and an exit window 418. The second face includes a non-transmissible region 412 and a partially transmissible region 416. The etalon 400 also includes four faces perpendicular to the front and back faces: a top 413, bottom 411, and sidewalls 417, 419.

The mirrors 422, 424 can be held in place by a mount (or mounts) that fix the location/orientation of the mirrors 422, 424 precisely with respect to the etalon 400. In particular, the mirror 422 can be mounted such that the optical path length traversed by a ray 420 during a round trip between the partially transmissible surface 416 and the mirror 422 is an integer multiple of the optical path length between successive reflections from the partially transmissible surface 416 while the light 420 is within the optical cavity 415 of the etalon 400. Similarly, the mirror 424 can be mounted such that the optical path length traversed by the ray 420 during a round trip between the partially transmissible surface 416 and the mirror 424 is an integer multiple of the optical path length between successive reflections from the partially transmissible surface 416.

Both the top mirror 422 and the bottom mirror 424 can be aligned such that the reflective surfaces of the mirrors 422, 424 define an angle with respect to the reflective surface 414. The angle 414 corresponds to the angle of reflection of the ray 420 within the etalon 400, which is based on the angle at which the etalon 400 is mounted with respect to light entering the entrance window 410. Thus, the mirrors 422, 424 may be mounted based on the orientation/position of the etalon 400 with respect to the optical axis of the optics that direct light into the etalon 400. In some examples, the mirrors 422, 424 may be arranged such that light 420 from the entrance/exit windows 410, 418 is reflected in a direction that is perpendicular to the mirror 422, 424. As such, light reflected back into the etalon 400 by the top mirror 422 maintains the same angle of reflection between the reflective surface 414 and the partially transmissible surface 416 during the downward pass through the etalon 400 that the light had during the initial upward pass through the etalon 400.

As shown in FIG. 4C, after the light 420 is reflected from the top mirror 422, the light is reflected back down the etalon 400 as indicated by ray 420'. The light propagating along ray 420' is reflected multiple times between the reflective surface 414 and the partially transmissible surface 416 before reaching the bottom mirror 424, at which point the light returns back up through the etalon 400 along another ray. The light can continue through the etalon 400 up and down until reaching near the sidewall 419, at which point any remaining light intensity can exit through exposed regions 424, 426 of the entrance/exit windows 410, 418 that are left uncovered by the mirrors 422, 424.

While the entrance window 410 extends along the entire width of the etalon 400, light enters the etalon 400 through a portion adjacent to the sidewall 417. To allow the light to undergo multiple passes through the etalon 400, the ray 420 is oriented slightly toward the opposite sidewall 419, such that the returning downward ray 420' is reflected by the bottom mirror 424 and does not exit through the exposed portion of the entrance window. In addition, the non-transmissible region 412, rather than extending across the entire width of the etalon 400 is situated only in the area that is directly across from the exposed region of the entrance window 410. As such, the non-transmissible region 412 reflects/absorbs any light that would not be reflected multiple times within the optical cavity 415 of the etalon 400, but does not interfere with the propagation of light that is making multiple upward/downward passes through the etalon 400.

On each upward and downward pass of the etalon 400, light is reflected multiple times from the partially transmissible surface 416, and each such reflection allows a portion of the light to be transmitted through, which transmissions contribute to the interference pattern. An example of the pattern of transmission points through the partially transmissible region 416 for the ray of light 420 is shown in FIG. 4E. Because each transmission point through the partially transmissible surface 416 of a given ray is delayed from a previous one by the same optical path length (or integer thereof), the transmissions each contribute to the interference pattern that can then be directed to a camera by a Fourier lens so as to detect wavelength contributions of the incident light 402.

Moreover, in comparison to the etalon 300 of FIG. 3, the multiple pass etalon 400 may be capable of generating many more individual points of transmission through the partially transmissible surface 416, which results in an interference pattern with greater definition for the wavelength-specific regions of constructive/destructive interference (i.e., a greater finesse). Because the etalon 400 is capable of providing far more reflections off of the partially transmissible surface for a given entrance angle, the tolerance of the parallel faces (e.g., less than 0.02 arcseconds of relative angle) is particularly important to creating interference patterns with high finesse. In addition, the reflectivity of the partially transmissible surface 416 can be much greater than in a comparable single pass etalon.

Figure 5A:
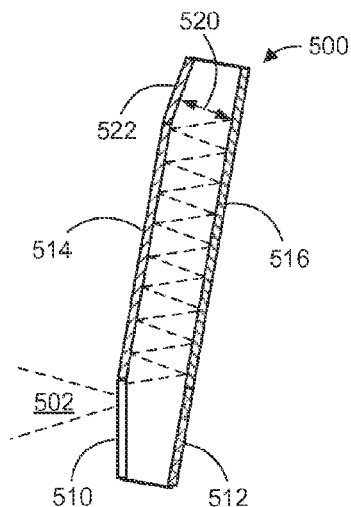
FIGS. 5A and 5B are views of an example VIPA that includes integrated aligned reflectors for directing light to undergo multiple passes through an etalon.
Figure 5B:
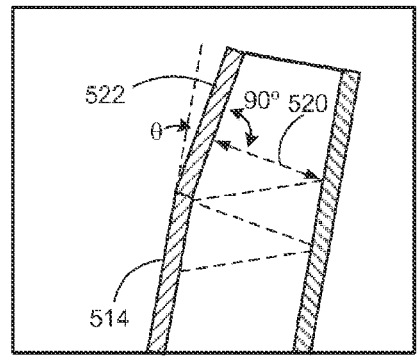
Figure 5C:
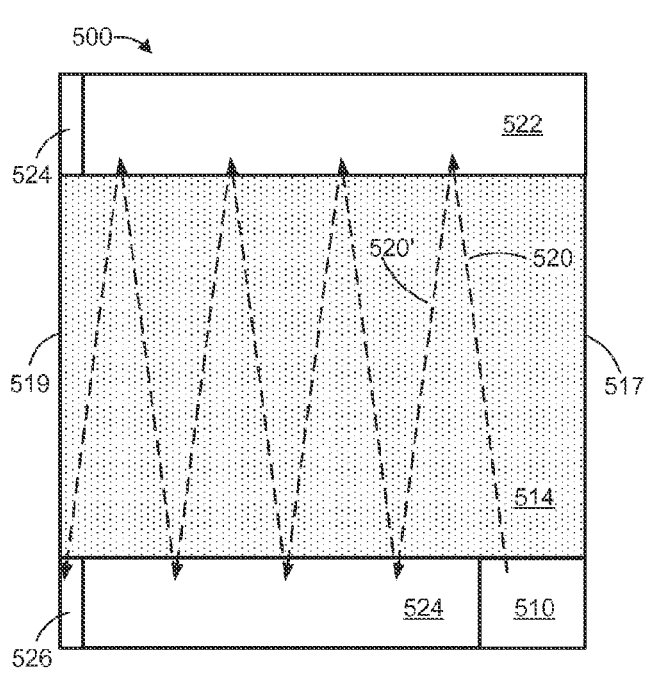
FIGS. 5C and 5D are views of a schematic diagram of the example etalon.
Figure 5D:
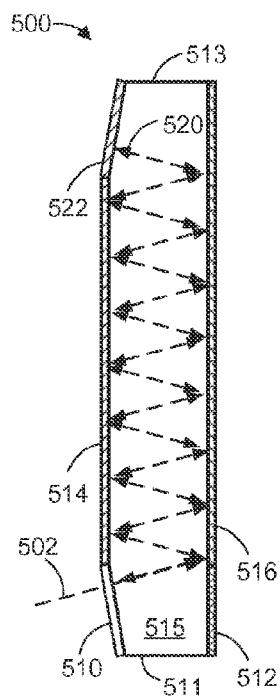

FIGS. 5A and 5B are views of an example VIPA that includes integrated aligned reflectors 522, 524 for directing light to undergo multiple passes through an etalon 500. FIGS. 5C and 5D are views of a schematic diagram of the example etalon 500. The etalon 500 can be similar in many respects to the etalon 400 of FIG. 4, and corresponding elements are generally labeled with a reference number one-hundred greater than the corresponding feature of the etalon 400, except for that the etalon 500 includes integrated reflectors 522, 524 rather than the externally mounted mirrors 422, 424. The etalon 500 includes a reflective surface 514 and a partially transmissible surface 516 that are aligned parallel with one another. The reflective surface 514 is on a front face of the etalon 500 that also includes an entrance window 510, and top/bottom reflectors 522, 524 adjacent to the reflective surface 514. The partially transmissible surface 516 is on a back face of the etalon 500 that also includes a non-transmissible region 512. The etalon 500 also includes four faces perpendicular to the reflective surface 514 and partially transmissible surface 516: a top 513, bottom 511, and sidewalls 517, 519.

The reflectors 522, 524 are angled sections of the first face of the etalon 500 configured to reflect light back toward the partially transmissible surface 516 and thus provide functionality similar to the mirrors 522, 524. The surface of the reflectors 522, 524 can define an angle θ with respect to the surface of the reflective surface 514 that is similar to the angle of the mirrors 422, 424 with respect to the reflective surface 414. However the reflectors 522, 524 are machined into the etalon 500 and may be formed by grinding/polishing the material of the etalon 500 to create the desired angle. In particular, the angle θ may be based on the angle at which the etalon 500 is oriented with respect to the incoming light 502 such that the ray of light 520 is reflected at approximately 90° from the two reflectors 522, 524. In addition, the entrance window 510 can be co-planar with the reflector 522, as shown in FIG. 5D. However, the entrance window 510 is a transmissible region and so the reflective coating and/or surface treatment applied to create the reflector 522 is patterned to not cover the entrance window 510. The non-transmissible region 512 is located opposite the entrance window 510. The exit regions 524, 526 can be transmissible regions adjacent to the sidewall 519, which allow any remaining light intensity that has propagated from the entrance window 510, near sidewall 517, to the opposite sidewall 519 via multiple up/down passes through the etalon 500 to exit the etalon 500. In some cases, the etalon 500 may include a single continuous exit region which extends along the entire height of the etalon 500, from the bottom 511 to the top 513, adjacent to the sidewall 519.

Figure 6A:
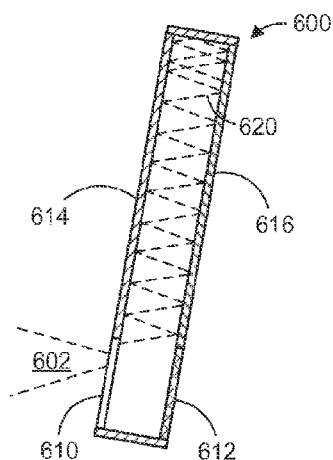
FIGS. 6A and 6B are views of an example VIPA that includes an integrated perpendicular reflector for directing light to undergo multiple passes through an etalon.
Figure 6B:
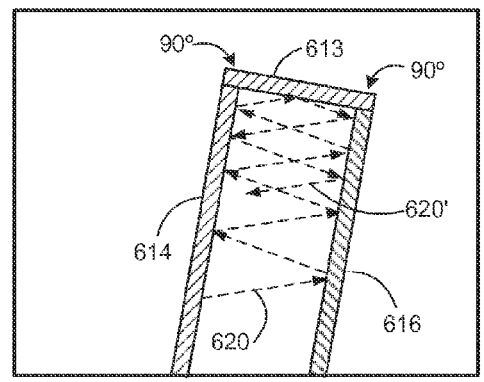
Figure 6C:
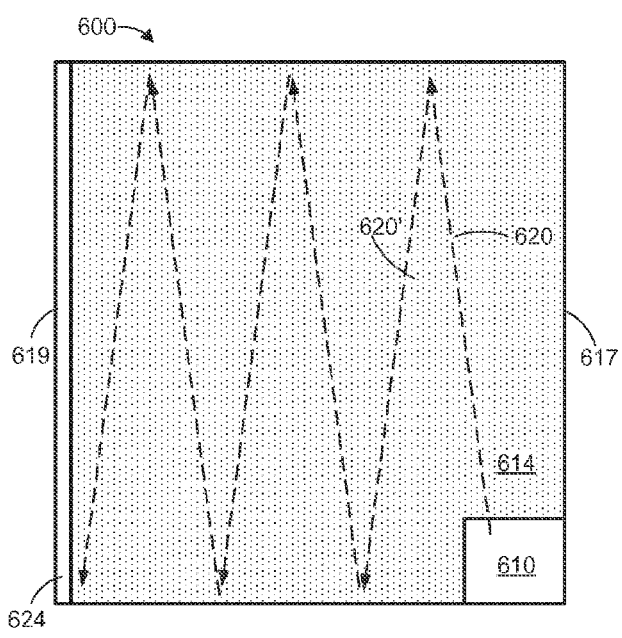
FIGS. 6C and 6D are views of a schematic diagram of the example etalon.
Figure 6D:
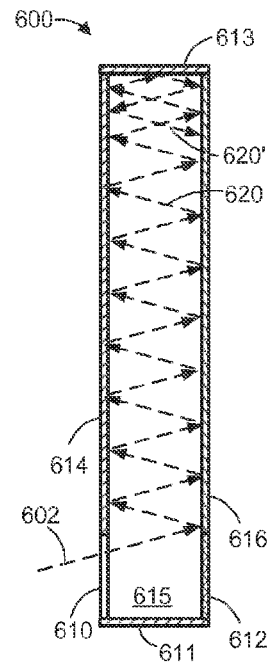

FIGS. 6A and 6B are views of an example VIPA that includes an integrated 90 degree reflector for directing light to undergo multiple passes through an etalon 600. FIGS. 6C and 6D are views of a schematic diagram of the example etalon 600. The etalon 600 can be similar in many respects to the etalon 400 and 500 of FIGS. 4-5, and corresponding elements are generally labeled with a reference number one-hundred greater than the corresponding feature of the etalon 500, except for that the etalon 600 includes reflective top 613 and bottom 611 and does not include reflectors or mirrors angled in accordance with the angle of orientation of the etalon 600. The etalon 600 includes a reflective surface 614 and a partially transmissible surface 616 that are aligned parallel with one another. The reflective surface 614 is on a front face of the etalon 600 that also includes an entrance window 610. The partially transmissible surface 616 is on a back face of the etalon 600 that also includes a non-transmissible region 612. The etalon 600 also includes four faces perpendicular to the reflective surface 514 and partially transmissible surface 616: a top 613, bottom 611, and sidewalls 617, 619.

The reflective surface 614 and partially transmissible surface 616 span the entire height of the etalon 600 (e.g., from the top 613 to the bottom 611) except for the transmissible portion of the entrance window 610 and the opposite non-transmissible region 612. The top 613 and bottom 611 are each oriented to reflect light back into the etalon 600 while maintaining an optical path length between subsequent reflections from the partially transmissible region 616. The top 613 and bottom 611 are each precisely perpendicular to the reflective surface 614 and partially transmissible surface 616 (e.g., within a tolerance error less than 0.02 arcseconds). As a result, light propagating upward through the optical cavity 615 of the etalon 600 along ray 620 is reflected by the top 613 with an angle directs the light to propagate back down the etalon 600 along ray 620' that maintains the angle of reflection with respect to the reflective surface 614 and the partially transmissible surface 616. Thus, just as in the etalons 400, 500, the light continues to make multiple upward/downward passes through the etalon 600 while being reflected back and forth between the reflective surface 614 and partially transmissible surface 616 multiple times on each pass. Each point of transmission for a given ray (e.g., the ray 620) on both upward and downward passes is therefore delayed from a previous point of transmission by a fixed optical path length, and the multiple points of transmission contribute to the interference pattern generated by the etalon 600 that indicates the wavelength components of the incident light 602. Finally, as shown in FIG. 6C, the exit window 624 may span the entire height of the etalon.

The example arrangements in FIGS. 4-6 provide three example arrangements for multiple pass etalons that include a reflective feature that directs light back through the etalon after completing a first pass through the etalon. On each pass, a given ray of light is reflected between parallel faces of the etalon multiple times. The reflective feature is configured to direct light back through the etalon such that an optical path length of light between passes (e.g., the optical path length of a roundtrip between the partially transmissible surface that includes) is an integer multiple of optical path lengths between subsequent reflections of the partially transmissible surface within the etalon. As such, points of transmission through the partially transmissible surface on different passes through the etalon have a constant phase delay with respect to each other and all contribute to the interference pattern generated by the multiple pass etalon. It is noted that while the reflective feature may be an externally aligned mirror, an integrated aligned reflector, and/or a perpendicular reflector, as in the examples provided here, other examples may also be possible.

FIGS. 7A and 7B are views of a schematic diagram of an example etalon 700 having mounting pins attached thereto. The etalon can be a multiple pass etalon such as any of the multiple pass etalons described above in connection with FIGS. 4-6. The mounting pins can be rods or pegs formed of a thermally stable material that are coupled to the sidewalls 717, 719 of the etalon 700, or perhaps integrally formed with the etalon 700. Mounting pin 730 can be adhered to the sidewall 717 and mounting pins 732, 734 can be adhered to the sidewall 719. A kinematic mount can then be used to mount the etalon 700 by placing etalon 700 such that each pin 730, 732, 734 contacts a corresponding kinematic mount point that fixes at least one degree of freedom of the etalon 700. However, the mount point can be configured so as to exert only local normal force on each of the mounting pins 730, 732, 734 and thereby avoid applying stress on the etalon 700 that is exerted across the body of the etalon 700. Such a mounting system desirably avoids creating shear stresses/forces on the etalon 700 with a tendency to distort the parallel alignment of the reflective surface 714 and partially transmissible surface 716.

Figure 8A:
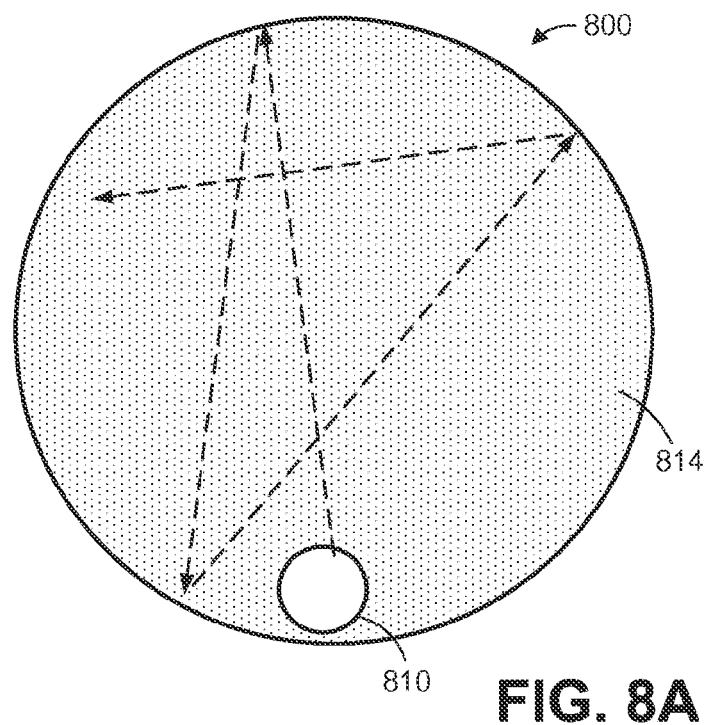
FIGS. 8A, 8B, and 8C are views of alternative shapes for etalons configured as multipass VIPAs.
Figure 8B:
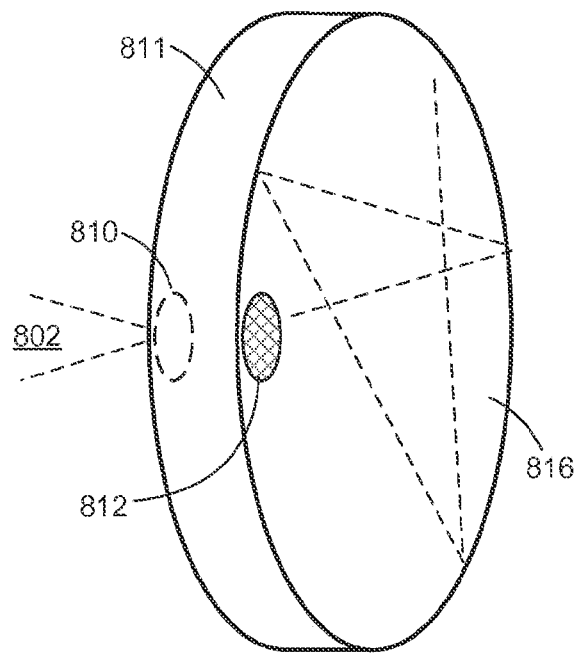
Figure 8C:
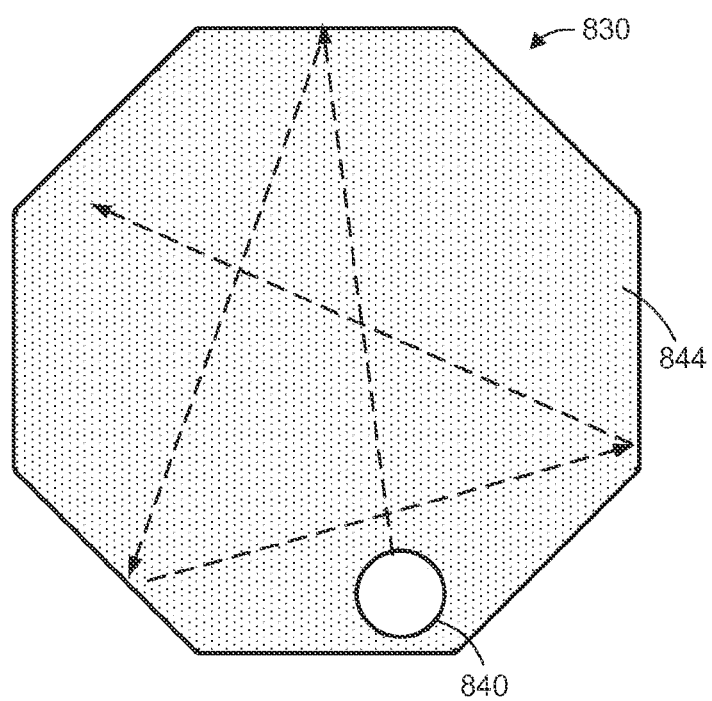

FIGS. 8A, 8B, and 8C are views of alternative shapes for etalons configured as multipass VIPAs. FIG. 8A shows a front face view of a circular etalon 800, and FIG. 8B is an aspect view of the circular etalon 800. The circular etalon 800 is shaped as a cylinder with two circular faces that are aligned parallel with one another. The front face, shown in FIG. 8A includes a reflective surface 814 and an entrance window 810. The entrance window 810 can be an area of the front face that is entirely surrounded by the reflective surface 814 or may be adjacent to a portion of a sidewall 811 of the etalon 810. The sidewall 811 can be perpendicular to both the reflective surface 816 and extend along the thickness of the etalon 800. The back face, visible in FIG. 8B includes the partially transmissible surface 816 and non-transmissible region 812. The non-transmissible region 812 is located immediately opposite the entrance window 810 so as to block (e.g., reflect and/or absorb) any of the incident light 802 that is not aligned to undergo multiple reflections between the reflective surface 814 and the partially transmissible surface 816.

A path of an example ray of light that enters the entrance window 810 is shown in FIGS. 8A and 8B. The ray is reflected multiple times between the reflective surface 814 and the partially transmissible surface 816 while propagating toward the sidewall 811. At the sidewall 811, the ray is reflected back into the etalon 800 while maintaining the angle of reflection of the ray with respect to the reflective surface 814 and partially transmissible surface 816. The reflection from the perpendicular sidewall 811 is similar to the reflection from the perpendicular top 613 and bottom 611 in the etalon 600. The ray of light may undergo multiple passes through the etalon 800 until the intensity of the incident light 802 has been substantially dissipated through the partially transmissible surface 814. In some cases, the etalon 800 may include an exit window on a portion of the front face to allow remaining light intensity to exit the etalon 800.

FIG. 8C is a front face view of a polygonal etalon 830. The polygonal etalon 830 includes a pair of octagonal faces that are aligned parallel to one another and sidewalls that extend perpendicular between the parallel faces. FIG. 8C shows the reflective surface 844 and the entrance window 840 of the etalon 830. The reflective surface 844 is parallel to a partially transmissible surface on the back face (not visible), which is opposite the reflective surface 844. Similarly, the entrance window 840 is located opposite a non-transmissible region on the back face, which light from contributing to the interference pattern unless it is aligned to undergo multiple reflections between the reflective surface 844 and partially transmissible surface. A path of an example ray of light is illustrated by the arrows in FIG. 8C. The path of the ray undergoes multiple passes across the etalon 830 while being reflected back and forth between the reflective surface 844 and the partially transmissible surface on each pass. The perpendicular sidewalls of the polygonal etalon 830 keep the light in phase, and maintain an angle of reflection with respect to the parallel surfaces, similar to the perpendicular sidewall 811 of the circular etalon 800.

Although the example systems and methods described herein may be directed to measuring biomechanical properties of the eye to plan, implement, and assess treatments of the eye, it is contemplated that aspects of the present disclosure may apply to analysis involving other body parts. For example, aspects of the system 100 described above may be employed in the field of cardiology where the cardio-vasculature is imaged. In such an application, the system may include a sample arm fiber that is coupled to a rotating fiber that is placed down a catheter. A 360 degree image of the lumen of the vessel is obtained. The fiber is then slowly withdrawn to obtain a 3D mapping of the vessel.

The present disclosure includes systems having processors (sometimes considered controllers) for providing various functionality related to processing information and determining results based on inputs. Generally, the processors (such as the processors 112 of the control system 110 described throughout the present disclosure and illustrated in the figures) may be implemented as a combination of hardware and software elements. The hardware aspects may include combinations of operatively coupled hardware components including microprocessors, logical circuitry, communication/networking ports, digital filters, memory, or logical circuitry. The processor may be adapted to perform operations specified by a computer-executable code (e.g., the program instructions 116), which may be stored on a computer readable medium (e.g., the data storage 114). The processors 112 may be implemented in any device, system, or subsystem to provide functionality and operation according to aspects of the present disclosure.

The processor(s) 112 may be a programmable processing device, such as an external conventional computer or an on-board field programmable gate array (FPGA) or digital signal processor (DSP) that executes software, or stored instructions. In general, physical processors and/or machines employed by embodiments of the present disclosure for any processing or evaluation may include one or more networked or non-networked general purpose computer systems, microprocessors, field programmable gate arrays (FPGA's), digital signal processors (DSP's), microcontrollers, and the like, programmed according to the teachings of the example embodiments of the present disclosure, as is appreciated by those skilled in the computer and software arts. The physical processors and/or machines may be externally networked with image capture device(s), or may be integrated to reside within the image capture device. Appropriate software can be readily prepared by programmers of ordinary skill based on the teachings of the exemplary embodiments, as is appreciated by those skilled in the software art. In addition, the devices and subsystems of the exemplary embodiments can be implemented by the preparation of application-specific integrated circuits or by interconnecting an appropriate network of conventional component circuits, as is appreciated by those skilled in the electrical art(s). Thus, the exemplary embodiments are not limited to any specific combination of hardware circuitry and/or software.

Stored on any one or on a combination of computer readable media, the example embodiments of the present disclosure may include software for controlling the devices and subsystems of the exemplary embodiments, for driving the devices and subsystems of the example embodiments, for enabling the devices and subsystems of the exemplary embodiments to interact with a human user, and the like. Such software can include, but is not limited to, device drivers, firmware, operating systems, development tools, applications software, and the like. Such computer readable media further can include the computer program product of an embodiment of the present disclosure for performing all or a portion (if processing is distributed) of the processing performed in implementations. Computer code devices of the example embodiments of the present disclosure can include any suitable interpretable or executable code mechanism, including but not limited to scripts, interpretable programs, dynamic link libraries (DLLs), Java classes and applets, complete executable programs, and the like. Moreover, parts of the processing of the exemplary embodiments of the present disclosure can be distributed for better performance, reliability, cost, and the like.

The processor(s) 112 may include, or be otherwise combined with, computer-readable media 114. Some forms of computer-readable media may include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the systems and methods of the present disclosure are described above and illustrated as being directed to measuring biomechanical properties and tomography information for a cornea, it should be understood that the systems and methods of the present disclosure can also be employed for other target features of the eye. For example, the systems and methods of the present disclosure can be additionally and/or alternatively employed to plan, implement, and assess treatments for an intraocular lens and/or a retina of the eye. Accordingly, the biomechanical data can be based on the Brillouin scattering measurements of the cornea, the intraocular lens and/or the retina, and the corneal tomography data can be more generally characterized as tomography data measured for the cornea, the intraocular lens, and/or the retina. It should thus be understood that the biomechanical data and the tomography data for the intraocular lens and/or the retina can be correlated based on the registration data to develop, implement, and/or assess treatment plans for the intraocular lens and/or the retina as described above for the corneal implementations of the present disclosure.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:

1. An optical device, comprising:
a reflective first surface;
a partially reflective/transmissible second surface parallel to the first surface, the second surface being spaced from the first surface to define an optical cavity therebetween, the optical cavity having a first end and a second end;
an entrance window disposed at the first end of the optical cavity and opposite the second surface, the entrance window configured to transmit light including light rays into the optical cavity and to allow the light rays to travel to the second surface, causing the light rays to be reflected between the first and second surfaces multiple times and to traverse the optical cavity toward the second end of the optical cavity in a first pass; and
a first reflective element disposed at the second end of the optical cavity and opposite the second surface, the first reflective element positioned and oriented to receive the light rays traveling from the second surface and along a direction determined by reflection of the light rays between the first and second surfaces during the first pass, the first reflective element configured to reflect the light rays further to the second surface after the first pass, causing the light rays to be further reflected between the first and second surfaces multiple times and to traverse the optical cavity toward the first end of the optical cavity in a second pass, the light rays traveling a first optical path length from the second surface to the first reflective element and back to the second surface, the light rays traveling a second optical path length from the second surface to the first surface and back to the second surface during the second pass, the first optical path length being an integer multiple of the second optical path,
wherein a portion of light from the light rays is transmitted through the second surface with each reflection at the second surface, the transmitted portions of light generating an interference pattern that provides spectral information for the light.

2. The optical device of claim 1, further comprising a second reflective element disposed at the first end of the optical cavity and opposite the second surface, the second reflective element configured to reflect the light rays to the second surface after the second pass, causing the light rays to be further reflected between the first and second surfaces multiple times and to traverse the optical cavity toward the second end of the optical cavity in a third pass, the light rays traveling a third optical path length from the second surface to the second reflective element and back to the second surface, the light rays traveling a fourth optical path length from the second surface to the first surface and back to the second surface during the third pass, the third optical path length being an integer multiple of the fourth optical path.

3. The optical device of claim 2, wherein the first reflective element and the second reflective element cause the light rays to traverse the optical cavity between the first and second ends in additional passes, the light rays reflecting between the first and second surfaces during each additional pass.

4. The optical device of claim 2, further comprising an exit window disposed at the second end of the optical cavity and opposite the second surface, wherein the light rays exit the optical cavity through the exit window.

5. The optical device of claim 4, wherein the optical cavity further includes a first side and a second side, the entrance window being further disposed at the first side of the optical cavity and the exit window being further disposed at the second side of the optical cavity, wherein the light ray further traverses the optical cavity from the first side to the second side with each pass from the first end to the second end until the light ray exits the optical cavity through the exit window.

6. The optical device of claim 4, further comprising a thermally stable substrate having a first face and a second face, the first face parallel to the second face,
wherein the reflective first surface, the entrance window, and the exit window are formed on the first face of the substrate,
the partially reflective/transmissible second surface is formed on the second face of the substrate, and
the optical cavity is defined within the substrate.

7. The optical device of claim 6, further comprising:
a transmissible third surface disposed at the first end of the optical cavity and formed on the first face of the substrate; and
a transmissible fourth surface disposed at the second end of the optical cavity and formed on the first face of the substrate,
wherein the first surface is disposed between the third and fourth surfaces,
the first reflective element is disposed across a first portion of the fourth surface and the exit window is defined by a second portion of the fourth surface across which the first reflective element is not disposed, and
the second reflective element is disposed across a first portion of the third surface and the entrance window is defined by a second portion of the third surface across which the second reflective element is not disposed.

8. The optical device of claim 7, wherein the first reflective element includes a first mirror coupled to the substrate and positioned across the first portion of the fourth surface, and the second reflective element includes a second mirror coupled to the substrate and positioned across the first portion of the third surface.

9. The optical device of claim 6, wherein the first reflective element is formed on a first angled portion of the first face of the substrate and the first reflective element is formed on a second angled portion of the first face of the substrate.

10. The optical device of claim 6, wherein the substrate includes:
a third face extending between the first face and the second face at the first end of the optical cavity, and
a fourth face extending between the first face and the second face at the second end of the optical cavity,
wherein the first reflective element is formed on the fourth face of the substrate, and the second reflective element is formed on the third face of the substrate.

11. An optical device, comprising:
a reflective first surface;
a partially reflective/transmissible second surface parallel to the first surface, the second surface being spaced from the first surface to define an optical cavity therebetween, the optical cavity having a first end and a second end;
an entrance window disposed at the first end of the optical cavity and opposite the second surface, the entrance window configured to transmit light including light rays into the optical cavity and to allow the light rays to travel to the second surface, causing the light rays to be reflected between the first and second surfaces multiple times and to traverse the optical cavity toward the second end of the optical cavity in a first pass;
a first reflective element disposed at the second end of the optical cavity and opposite the second surface; and
a second reflective element disposed at the first end of the optical cavity and opposite the second surface,
wherein the first reflective element and the second reflective element cause the light rays to traverse the optical cavity between the first and second ends in additional passes, the light rays reflecting between the first and second surfaces during each additional pass,
wherein the light rays travel a first optical path length from the second surface to the first reflective element and back to the second surface, the light rays travel a second optical path length from the second surface to the first surface and back to the second surface during the second pass, the first optical path length is an integer multiple of the second optical path,
wherein the light rays travel a third optical path length from the second surface to the second reflective element and back to the second surface, the light rays travel a fourth optical path length from the second surface to the first surface and back to the second surface during the third pass, the third optical path length is an integer multiple of the fourth optical path, and
wherein a portion of light from the light rays is transmitted through the second surface with each reflection at the second surface, the transmitted portions of light generating an interference pattern that provides spectral information for the light.

12. A system that determines biomechanical properties of corneal tissue, comprising:
a light source configured to provide an incident light;
a confocal microscopy system configured to scan the incident light across a plurality of cross-sections of the corneal tissue, the incident light being reflected by the plurality of cross-sections of corneal tissue as scattered light;
a spectrometer configured to receive the scattered light and provide spectral information for the received scattered light; and
one or more processors configured to determine a Brillouin frequency shift from the spectral information and to generate a three-dimensional profile of the corneal tissue according to the determined Brillouin frequency shift, the three-dimensional profile providing an indicator of one or more biomechanical properties of the corneal tissue,
wherein the spectrometer includes:
an optical device including:
a reflective first surface;
a partially reflective/transmissible second surface parallel to the first surface, the second surface being spaced from the first surface to define an optical cavity therebetween, the optical cavity having a first end and a second end;
an entrance window disposed at the first end of the optical cavity and opposite the second surface, the entrance window configured to transmit the scattered light including light rays into the optical cavity and to allow the light rays to travel to the second surface, causing the light rays to be reflected between the first and second surfaces multiple times and to traverse the optical cavity toward the second end of the optical cavity in a first pass; and
a first reflective element disposed at the second end of the optical cavity and opposite the second surface, the first reflective element positioned and oriented to receive the light rays traveling from the second surface and along a direction determined by reflection of the light rays between the first and second surfaces during the first pass, the first reflective element configured to reflect the light rays further to the second surface after the first pass, causing the light rays to be further reflected between the first and second surfaces multiple times and to traverse the optical cavity toward the first end of the optical cavity in a second pass, the light rays traveling a first optical path length from the second surface to the first reflective element and back to the second surface, the light rays traveling a second optical path length from the second surface to the first surface and back to the second surface during the second pass, the first optical path length being an integer multiple of the second optical path,
wherein a portion of light from the light rays is transmitted through the second surface with each reflection at the second surface, the transmitted portions of light generating an interference pattern that provides the spectral information for the scattered light; and
a camera configured to detect the interference pattern from the optical device.

13. The system of claim 12, wherein the spectrometer optical device further includes a second reflective element disposed at the first end of the optical cavity and opposite the second surface, the reflective element configured to reflect the light rays to the second surface after the second pass, causing the light rays to be further reflected between the first and second surfaces multiple times and to traverse the optical cavity toward the second end of the optical cavity in a third pass, the light rays traveling a third optical path length from the second surface to the second reflective element and back to the second surface, the light rays traveling a fourth optical path length from the second surface to the first surface and back to the second surface during the third pass, the third optical path length being an integer multiple of the fourth optical path.

14. The system of claim 13, wherein the first reflective element and the second reflective element cause the light rays to traverse the optical cavity between the first and second ends in additional passes, the light rays reflecting between the first and second surfaces during each additional pass.

15. The system of claim 13, wherein the spectrometer optical device further includes an exit window disposed at the second end of the optical cavity and opposite the second surface, wherein the light rays exit the optical cavity through the exit window.

16. The system of claim 15, wherein the optical cavity further includes a first side and a second side, the entrance window being further disposed at the first side of the optical cavity and the exit window being further disposed at the second side of the optical cavity, wherein the light ray further traverses the optical cavity from the first side to the second side with each pass from the first end to the second end until the light ray exits the optical cavity through the exit window.

17. The system of claim 15, wherein the spectrometer optical device further includes a thermally stable substrate having a first face and a second face, the first face parallel to the second face,
- wherein the reflective first surface, the entrance window, and the exit window are formed on the first face of the substrate,
- the partially reflective/transmissible second surface is formed on the second face of the substrate, and
- the optical cavity is defined within the substrate.

18. The system of claim 12, wherein the spectrometer further includes:
- a collimating lens configured to collimate the scattered light; and
- a focusing lens configured to direct the collimated light to the entrance window of the optical device.

19. The system of claim 12, wherein the spectrometer further includes a Fourier lens aligned with the optical device and configured to direct the interference pattern to the camera in a fringe pattern separating wavelengths of the scattered light at respective angles, wherein the spectrometer camera includes a light-sensitive array disposed at an imaging plane of the Fourier lens, each element of the light sensitive array sampling a respective angle of the fringe pattern, each angle providing an intensity for the respective wavelength.

20. The system of claim 12, wherein the spectrometer includes a mount for receiving the optical device, wherein the optical device further includes pins that contact mount points of the mount to minimize shear forces on the optical device.

* * * * *